United States Patent [19]

Hammer et al.

[11] Patent Number: 5,489,742

[45] Date of Patent: Feb. 6, 1996

[54] TRANSGENIC RATS AND ANIMAL MODELS OF INFLAMMATORY DISEASE

[75] Inventors: Robert E. Hammer, Euless; Joel D. Taurog, Dallas, both of Tex.

[73] Assignee: Board of Regents, the University of Texas System, Austin, Tex.

[21] Appl. No.: 724,974

[22] Filed: Jun. 27, 1991

Related U.S. Application Data

[63] Continuation of Ser. No. 602,131, Oct. 23, 1990, abandoned.

[51] Int. Cl.$^6$ .......................... C12N 15/00; A61K 39/00; A61K 49/00
[52] U.S. Cl. .................... 800/2; 435/172.3; 800/DIG. 1
[58] Field of Search ..................................................... 800/2

[56] References Cited

U.S. PATENT DOCUMENTS 4,736,866  4/1988  Leder et al. ................................ 800/1

FOREIGN PATENT DOCUMENTS

91/01140  2/1991  WIPO .

OTHER PUBLICATIONS

Hammer et al., "Spontaneous Inflammatory Disease in Transgenic Rats Expressing HLA–B27 and Human $\beta_2$m: An Animal Model of HLA–B27–Associated Human Disorders," Cell, 63:1099–1112, (1990).
The New York Times, "Researchers Genetically Alter Rats to Mimic Human Arthritis," (Nov. 30, 1990).
The Wall Street Journal, "Scientific Team Develops Arthritic Rats, Bolstering Belief that Gene Is to Blame," (Nov. 30, 1990).
Hammer et al., Abstract, "Transgenic Rats Expressing HLA–B27 and Human $B_2$–Microglobulin," *American College of Rheumatology, 54th Annual Scientific Meeting*, Seattle, (Oct. 27–Nov. 1, 1990).
Hammer et al., Abstract, "Spontaneous Arthritis In Transgenic Rats Expressing HLA–B27", American Society for Histocompatibility and Immunogenetics, 16th Annual Meeting, Los Angeles, (Nov. 3–7, 1990).
Hammer et al., Abstract, "Transgenic Rats Expressing HLA–B27 And Human $\beta_2$–Microglobulin," American Federation For Clinical Research, Washington, D.C. (May 4–7, 1990).
El–Zaatari et al., "In Vitro Mutagenesis of HLA–B27: Amino Acid Substitutions at Position 67 Disrupt Anti–B27 Monoclonal Antibody Binding in Direct Relation to the Size of the Substituted Side Chain," J. of Immunology, 144:1512–1517, (1990).
Egorov, I. K. and C. S. David (Eds.), *Transgenic Mice Mutants in MHC Research*, Springer–Verlag, (1990), Not a Reference.
Ivanyi et al., "Male Sterility in HLA–B27–Transgenic Mice," *Transgenic Mice and Mutants in MHC Research*, Egorov, I. K. and C. S. David (Eds.) Springer–Verlag, pp. 161–164, (1990).
Mullins et al., "Fulminant hypertension in transgenic rats harboring the mouse Ren–2 gene," Nature, 344:541–544, (1990).
Luthra et al., "HLA–B27 and Arthritis," *Transgenic Mice and Mutants in MHC Research*, Egorov, I. K. and C. S. David (Eds.), Springer–Verlag, pp. 259–267, (1990).
Taurog et al., "HLA–B27 Transgenic Mice as Potential Models of Human Disease," *Transgenic Mice and Mutants in MHC Research*, Egorov, I. K. and C. S. David (Eds.), Springer–Verlag, pp. 268–275, (1990).
Khan, "An Overview Of The HLA System," SPINE:State of the Art Reviews, 4(3):595–605, (1990).
Taurog, "Molecular Genetics Of HLA–B27," *SPINE:State of the Art Reviews, 4(3):607–615, (1990)*.
Bodmer et al., "Nomenclature for Factors of the HLA System, 1989," Human Immunology, 28:326–342, (1990).
Newman, "The Difficulties of Patenting Transgenic Animals," ASM News, 56(5):252–253, (1990).
Taurog, "Genetics and immunology of the spondyloarthropathies," Current Opinion in Rheumatology, 1:144–150, (1989).
Oudejans et al., "Lack Of Expression of HLA–B27 Gene In Transgenic Mouse Trophoblast," J. Exp. Med., 169:447–459, (1989).
Taurog et al., "HLA–B27 In Inbred And Non–Inbred Transgenic Mice," J. of Imm., 141(11):4020–4023, (1988).
Taurog et al., "In Vitro Mutagenesis of HLA–B27," J. Clin. Invest., 82:987–992, (1988).
Armstrong et al., "Superovulation of Immature Rats by Continuous Infusion of Follicle–Stimulating Hormone," B. of Reproduction, 39:511–518 (1988).
Krimpenfort et al., "Crosses of two independently derived transgenic mice demonstrate functional complementation of the genes encoding heavy (LHA–B27) and light ($\beta_2$–microglobulin) chains of HLA Class I antigens," EMBO Journal, 6(6):1673–1676, (1987).
Kievits et al., "HLA–restricted recognition of viral antigens in HLA transgenic mice," Nature, 329:447–449, (1987).

(List continued on next page.)

Primary Examiner—Suzanne E. Ziska
Attorney, Agent, or Firm—Arnold, White & Durkee

[57] ABSTRACT

The present disclosure relates in general to the generation of transgenic rats having incorporated into their genome a selected transgene. However, in particular aspects, the present invention concerns the introduction of an HLA-B27 or DR4 gene into the rat genome, or that of other non-human mammals other than mice, to produce transgenic lines having the propensity to spontaneously develop an inflammatory disease trait including inflammatory lesions of the peripheral or axial joints, gastrointestinal tract, genital tract, nails, skin, eye, lungs or heart. This is preferably achieved through the co-introduction of a human HLA-B27 gene together with a human beta-2 microglobulin gene into fertilized eggs from superovulated female rats, which eggs are then brought to term in a pseudopregnant female. The resulting offspring are employed to generate transgenic lines from which lines exhibiting the desired traits are selected and maintained.

7 Claims, 7 Drawing Sheets

OTHER PUBLICATIONS

Leder et al., "Consequences of Widespread Deregulation of the c–myc Gene in Transgenic Mice: Multiple Neoplasms and Normal Development," Cell, 45:485–495, (1986).

Lovell–Badge, "Transgenic Animals: New advances in the field," Nature, 315:628, (1985).

Hammer et al., "Production of transgenic rabbits, sheep and pigs by microinjection," Nature, 315(6021):680–683, (1985).

Brinster et al., "Factors affecting the efficiency of introducing foreign DNA into mice by microinjecting eggs," Proc. Natl. Acad. Sci., 82:4438–4442, (1985).

Lawrence et al., "Transgenic HLA–DRα Faithfully Reconstitutes IE–Controlled Immune Functions and Induces Cross–Tolerance to Eα in Eα$^0$ Mutant Mice," Cell, 58:583–594 (1989) Published in USA.

Sarvetnick et al., "Insulin–Dependent Diabetes Mellitus Induced in Transgenic Mice by Ectopic Expression of Class II MHC and Interferon–Gamma", Cell, 52:773–782 (1988) Published in USA.

Ignat'eva, T. V. and Golinskii, G. F., "Transgenic rats expressing human growth hormone gene as a model of some types of diabetes" Chemical Abstracts, 114:435(2) (1991).

International Search Report Published in Europe.

Ignat'eva, T. V., and Golinskii, F. G., "Transgenic Rats Expressing Human Growth Hormone Gene as a Model of Some Types of Diabetes," *Biopolimery I Kletka*, 6(2):24–31, 1990.

Handbook of Animal Models for the Rheumatic Diseases, vol. I, Robert A. Greenwald, M.D., and Herbert S. Diamond, M.D., Eds., CRC Press, Inc., 1988.

Brahn & Trentham, "Arthritis Induced by Total Lymphoid Irradiation," *Handbook of Animal Models for the Rheumatic Diseases*, vol. I, pp. 83–91, 1988.

Cannon & Ward, "Inflammation Induced by 6–Sulfanilamidoindazole," *Handbook of Animal Models for the Rheumatic Diseases*, vol. I, pp. 93–99, 1988.

Cremer, "Type II Collagen–Induced Arthritis in Rats," *Handbook of Animal Models for the Rheumatic Diseases*, vol. I, pp. 17–27, 1988.

Forrest, et al., "The Subcutaneous Air–Pouch Model of Inflammation," *Handbook of Animal Models for The Rheumatic Diseases*, vol. I, pp. 125–134, 1988.

Kerwar, et al., "Comparative Studies Between Adjuvant, Type II Collagen, and Streptococcal Cell Wall–Induced Arthritis in Rats," *Handbook of Animal Models for the Rheumatic Diseases, vol. I, pp. 49–52, 1988.*

Lehman, "*Lacobacillus casei* Cell–Wall–Induced Arthritis in Rats," *Handbook of Animal Models for the Rheumatic Diseases*, vol. I, pp. 41–47, 1988.

Ridge, et al., "Passive Collagen Arthritis Induced by Affinity Purified Anticollagen IgG," *Handbook of Animal Models for the Rheumatic Diseases*, vol. I, pp. 29–32, 1988.

Whitehouse, "Adjuvant–Induced Polyarthritis in Rats," *Handbook of Animal Models for the Rheumatic Diseases*, vol. I, pp. 3–16, 1988.

Wilder, "Streptococcal Cell Wall–Induced Polyarthritis in Rats," *Handbook of Animal Models for the Rheumatic Diseases*, vol. I, pp. 33–40, 1988.

Sries et al PNAS 82:5165, 1985.

TRANSGENIC RATS AND ANIMAL MODELS OF INFLAMMATORY DISEASE

The U.S government may own certain rights in the present invention pursuant to NIH grant number AR09989.

The present application is a continuing application of U.S. Ser. No. 602,131 filed Oct. 23, 1990, now abandoned and all benefits under 35 U.S.C 120 are hereby expressly claimed.

BACKGROUND OF THE INVENTION

1. Field of the Invention

This invention relates generally both to transgenic rats and to animal models of human disease, particularly to transgenic animals which can serve as animal models of human inflammatory diseases. In specific aspects, the invention relates to transgenic rats which have the human HLA-B27 gene inserted into their genome, which develop symptomology not unlike that seen in B27-related disorders in humans.

2. Description of the Related Art

It has become evident that major histocompatibility genes play a role in the development, or propensity for the development, of a number of human inflammatory diseases, including the rheumatic diseases rheumatoid arthritis and the spondyloarthropathies. For example, several human inflammatory diseases of unknown etiopathogenesis are now known to be genetically associated with certain HLA alleles (Tiwari et al., 1985). While in no case has the mechanism underlying such an association yet been elucidated, it is likely that such elucidation will provide new insights into the pathogenesis of a number of hitherto puzzling human diseases.

The disorders commonly classified as spondyloarthropathies share a number of clinical similarities (Calin, 1984; Moll et al., 1974). These disorders can be conveniently separated into two groups, including those with an increased prevalence among B27+ individuals and those without an association with B27 (Tiwari et al., 1985). The first group includes ankylosing spondylitis (AS), reactive arthritis, and the spondylitis associated with psoriasis or inflammatory bowel disease; the second group includes the peripheral arthritis associated with psoriasis or inflammatory bowel disease. The inflammatory eye disease, acute anterior uveitis, is strongly associated with HLA-B 27, but can occasionally be found with any of these rheumatic disorders in the absence of B27. In none of these disorders is the etiology well understood, although any concept of pathogenesis should include a central role of the HLA-B27 molecule.

Ankylosing spondylitis is an inflammatory disorder of unknown etiology that primarily affects the axial skeleton; peripheral joints and extraarticular structures may also be involved (Taurog and Lipsky 1990). The disease usually begins in the second or third decade; the prevalence in men is approximately three times that in women. It is considered the prototype of the group of disorders collectively referred to as the spondyloarthropathies, which includes ankylosing spondylitis, reactive arthritis, psoriatic arthritis, psoriatic spondylitis, enteropathic arthritis, and enteropathic spondylitis. In Europe, AS is often referred to by the eponyms Marie-Strümpell disease or Bechterew disease.

AS shows a striking association with the presence of the histocompatibility antigen HLA-B27. The disease occurs throughout the human populations of the world in proportion to the prevalence of this antigen. In North American Caucasians, the prevalence of HLA-B27 in the general population is 7%, whereas over 90% of patients with AS have inherited this antigen (Brewerton et al. 1973; Schlosstein et al. 1973). The association with HLA-B27 is independent of disease severity. In large population surveys, 1–2% of adults inheriting HLA-B27 have been found to have AS. In contrast, in families of B27+ patients with AS, 10–20% of adult first degree relatives inheriting HLA-B 27 have been found to have the disease. The concordance rate in identical twins is estimated to be 60% or less. These epidemiologic findings indicate that both genetic and environmental factors play a role in the pathogenesis of the disease, and that the genetic factors probably include genes in addition to HLA-B27. Secondary forms of AS occur in individuals suffering from inflammatory bowel disease (enteropathic spondylitis) or psoriasis (psoriatic spondylitis).

Reactive arthritis refers to acute nonpurulent arthritis complicating an infection elsewhere in the body. In recent years, the term has been used primarily to refer to spondyloarthropathies following enteric or ufogenital infections and occurring predominantly in individuals with the histocompatibility antigen HLA-B27. Included in this category is the constellation of clinical findings often referred to as Reiter's syndrome.

Reactive arthritis in human occurs following enteric infection with a variety of gram negative bacteria, including *Shigella flexneri*, Salmonella species, *Yersinia enterocolitica* and *pseudotuberculosis*, and *Campylobacter jejuni* (Keat, A., 1983; Calin, A., 1984, Toivanen and Toivanen 1988; Taurog and Lipsky 1990). The mechanism by which these infections trigger arthritis is completely unknown. In general, the organisms cannot be cultured from inflamed synovial tissue, although there have been recent observations of bacterial antigens found in synovium following reactive arthritis (Keat et al. 1987; Granfors et al., 1989; Granfors et al., 1990 ).

It is widely assumed that the B27 molecule itself is involved in the pathogenesis of AS and reactive arthritis, although formal proof of this in humans is still lacking. Two types of evidence support this hypothesis. First, genetic and epidemiologic studies provide strong indirect evidence for involvement of B27 in AS (reviewed in Khan, 1988). Second, several studies have suggested antigenic cross-reactivity between the B27 molecule and various enteric organisms, some of which are implicated in triggering reactive arthritis (Raybourne et al., 1988; Chen et al., 1987; Schwimmbeck et al., 1987; Stieglitz, 1989; Yu, 1989).

Elucidation of the molecular basis of the B27-associated diseases is of interest because it might lead to effective prevention and therapy of these relatively common disorders that cause considerable morbidity and disability in otherwise healthy young adults. Such elucidation would likely provide significant insight into other common inflammatory diseases, and it may also contribute to a broader understanding of the function of class I MHC molecules in health and disease. One of the principal reasons behind the inability to provide answers to these important questions has been the unavailability of an animal model for B27 associated disease. Attempts have been made to develop such a model in mice through the transgenic introduction of the B27 gene into the mouse genome (Taurog et al. 1988a; Krimpenfort et al., 1987; Nickerson et al., 1990; Weiss et al., 1990). These efforts were successful in producing transgenic mice which expressed the incorporated HLA-B27 gene. However, despite physiologically normal function of the B27 gene product in mice (Kievits et al., 1987; Taurog et al., 1988a), and despite a reported influence of the B27 transgene on the course of an experimental bacterial infection (Nickerson et al., 1990), no faithful reproduction of any of the features of B27-associated human disease has been reported in B27 transgenic mice (Taurog et al., 1990, Arnold and Hämmerling, 1991).

Rheumatoid arthritis is a chronic, immune-mediated inflammatory disease that primarily affects the joints and their supporting structures, although the disease sometimes involves other organs and tissues such as the eyes, lungs, heart, and skin (Harris, 1990). This common disease produces profound morbidity and excess mortality in an estimated 1% of the population (Lawrence et al, 1989).

The alloantigen HLA-DR4 is highly associated with human rheumatoid arthritis (Stastny, 1978). At least eight subtypes of this alloantigen have been identified, including Dw4, Dw10, Dw13.1, Dw13.2, Dw14.1, Dw14.2, Dw15 and Dw "New" (Gao et al., 1990a,1990b). The Dw4 subtype ("DR4,Dw4") is the one most closely associated with rheumatoid arthritis.

Individuals possessing this subtype of DR4 have a risk of developing rheumatoid arthritis about five fold greater than individuals who lack DR4,Dw4 (Zoschke and Segall 1986; Gao et al., 1990b).

As with the B27-related disorders, the availability of an animal model of rheumatoid arthritis would prove instrumental in the development of treatment modalities and protocols, and indeed in the identification of novel agents for the treatment of this important disease. Unfortunately, the development of an animal model closely resembling rheumatoid arthritis has not been previously described.

Various animal models of human diseases have been enabled through the development of transgenic species exhibiting the desired traits. For example, U.S. Pat. No. 4,736,866 to Leder et al. describes technology for the development of transgenic mice having an activated oncogene introduced into the animal's genome. However, while transgene technology has been generally applicable to non-human animals such as mice, cows, pigs, guinea pigs, rabbits, sheep, chickens and even fish, transgenic introduction has proven difficult in some species such as rats, hamsters and guinea pigs.

Due to the widespread use of rats in biomedical research, the development of methods for producing transgenic rats would represent a significant advance. For the study of B27-associated and perhaps even DR4-associated rheumatoid arthritis disease in animals, the advantage of using transgenic rats in addition to mice is at least two-fold; first, arthritis is more readily inducible in rats than in mice; and, second, there are more conventional experimental models of arthritis in rats than in mice in which to study the influence of the B27 gene.

The development of an animal model of B27-associated or DR4associated disease in which all of these difficulties are circumvented would represent a significant advance in the understanding of this group of human disorders. For example, such models could provide a direct means for screening new anti-arthritic compounds or compounds which have the ability to treat symptoms of the various diseases, such as in the identification of new anti-inflammatory, anti-arthritic agents, anti-psoriatic agents, agents for the treatment of spondylitis, and the like. Moreover, on a scientific level, such a model could answer many of the questions which have arisen from our lack of information regarding these diseases.

SUMMARY OF THE INVENTION

The present invention addresses at least some of the shortcomings or disadvantages of the prior art by providing an animal model of inflammatory disease, and in particular, for the first time, transgenic rats having at least one selected transgene incorporated into their genome. As used herein, the phrase "incorporated into its genome" is intended to refer to rats or other mammals which have a selected transgene introduced into their germ cells and/or somatic cells such that it is stably incorporated and is capable of carrying out a desired function. The term "genome" is intended to include the entire DNA complement of an organism, including the nuclear DNA component, chromosomal or extrachromosomal DNA, as well as the cytoplasmic domain (e.g., mitochondrial DNA). Thus, the present invention contemplates that one or more transgenes may be stably incorporated into an organism's germ cells or somatic cells, in a functional form, and achieve a desired effect, e.g., such as conferring a selected trait onto the transgenic animal.

It is a general object of the present invention to provide animal models of various inflammatory diseases which are in some way associated with the expression of one or more genes encoding major histocompatibility antigens, through the preparation of transgenic animals having one or more major histocompatibility genes introduced into their genomes. For example, it is an object to provide an animal model of spontaneous inflammatory disease through the generation of transgenic animals having the HLA-B27 gene introduced into their genome. Moreover, it is proposed that an animal model of rheumatoid arthritis may be achieved through the transgenic introduction of class II genes such as the genes encoding the alloantigen HLA-DR4, particularly the Dw4 subtype.

Thus, a particular focus of the present invention is the generation of transgenic rats or other mammals which, by virtue of incorporation of an HLA-B27 transgene, have a propensity to spontaneously develop an inflammatory disease trait including inflammatory lesions of the peripheral or axial joints, gastrointestinal tract, genital tract, nails, skin, eye, lungs or even heart. The inventors have discovered that, unlike in mouse where incorporation of a B27 allele does not effect traits such as these, when one applies similar technology to the transgenic introduction of a B27 gene into rats, the selected rats receiving the transgene will exhibit one or more of these traits, typically within about 2 months to about 6 months following birth.

Moreover, it is another particular focus of the present invention to provide transgenic animals which, by virtue of the introduction of an HLA-DR4 transgene, particularly a Dw4 subtype of such a gene, will exhibit one or more symptoms of rheumatoid arthritis, such as arthritis, tendinitis, or even vasculitis.

As used herein, the term "transgene" is intended to refer broadly to the introduction of any desired DNA sequence into the animal's genome, including but not limited to genes or DNA sequences which are perhaps not normally present in the genome, genes which are present, but not normally transcribed and translated ("expressed") in a given genome, or any other genes or DNA sequences which one desires to introduce into the genome. This may include genes which may normally be present in the nontransgenic genome but which one desires to have altered in expression, or which one desires to introduce in an altered or variant form.

Although in certain aspects the invention relates generally to transgenic rats having any selected transgene incorporated into its genome, in certain embodiments, the invention concerns the incorporation of a major histocompatibility gene, or a functional mutant, variant, or derivative of such a gene. The phrase, "functional mutant, variant or derivative of such a gene" is intended to refer to any variant, mutant or derivative of a major histocompatibility gene which will nevertheless achieve the function of such a gene or an otherwise desirable effect. For example, it is well known that many allelic variations of MHC genes occur in nature, and that such variants will typically achieve a desired effect, whether the effect be one of the same overall biological function or perhaps even a somewhat different biological function. Furthermore, techniques are available for introducing man-made sequence variations into selected genes, which variations may confer on the gene new properties or an augmentation or reduction of an existing property or properties. Thus, the present invention is intended to include within its scope the use of mutants, variants, or derivatives of selected transgenes.

It is proposed that those of skill in the art who desire to introduce a major histocompatibility gene into a rat or other mammal in accordance with the present invention will find particular benefit through the introduction of human class I major histocompatibility gene, such as a gene from the HLA-A, HLA-B, or HLA-C locus. The HLA class I molecules are the classical transplantation antigens, encoded in the highly polymorphic HLA-A, B and C loci of the human MHC. The HLA class I molecules are composed of an MHC-encoded highly polymorphic, glycoprotein heavy or alpha chain non-covalently bound to a much smaller, non-MHC-encoded light or β chain, termed $\beta_2$-microglobulin. The class I genes have been studies extensively, and the genes for many of these molecules have been cloned and are therefore now available to the art for use in connection with the present invention (Klein 1986; Parham et al. 1988).

Where one intends to develop an animal model for human inflammatory disease, a preferred human class I major histocompatibility gene is an HLA-B27 gene, or functional mutant, variant or derivative thereof. The inventors have found that through introduction of an HLA-B27 transgene into the genome of a rat, one can develop therefrom a rat line which exhibits one or more spontaneous inflammatory disorders such as discussed above. It is specifically intended that the various well-characterized allelic variations of the B27 gene are included within the scope of the invention, as well any functional mutant, variant or derivative of such a gene. For example, it is known that the B27 gene can be mutagenized through the application of in vitro mutagenesis, and the resultant mutant HLA-B27 gene remains functional (See, e.g., Taurog and El-Zaatari, 1988; El-Zaatari, et al, 1990).

In other particular aspects, it is contemplated that advantages in accordance with the invention will be realized through the introduction of the HLA-B7 gene or functional mutant, variant or derivative thereof. Although the B7 gene is not as closely correlated with human disease as the B27 gene, it has nonetheless been implicated in reactive arthritis and ankylosing spondylitis. Furthermore, the B7 gene is serologically cross-reactive with the B27 gene product, and they are both members of the so-called B7-cross reactive group of HLA-B alleles.

Other class I genes which may be of particular use as transgenes in the practice of the present invention include the Cw6 and B38 genes. These genes may be of particular use because of their association with psoriasis vulgaris and psoriatic arthritis, respectively.

In that the gene products of the class I genes, when expressed on the surface of a cell, are associated with a $\beta_2$-microglobulin or light chain, it is proposed in preferred aspects of the invention that one may typically employ, in combination with the class I transgene, a human $\beta_2$-microglobulin gene or functional mutant, variant or derivative thereof. While the precise function of the associated $\beta_2$-microglobulin is not entirely clear, it is believed that an associated $\beta_2$-microglobulin is needed in order for the class I product to be expressed at the cell surface and function biologically. While it may be possible to rely upon the $\beta_2$-microglobulin gene which will inherently be present in the genome of the transgenic animal, one will most often desire to employ in combination with the class I gene a human $\beta_2$-microglobulin transgene which has been incorporated along with a human class I gene into the animal's genome. This is because the human $\beta_2$-microglobulin diverges by up to 30% in amino acid sequence homology from the rat $\beta_2$-microglobulin gene. Association of the human heavy chain with a mouse or rat $\beta_2$-microglobulin might therefore result in a less than optimally functional complex.

It will be appreciated upon practicing the present invention that not all transgenic animals which have an incorporated B27 gene will go on to develop symptoms of an inflammatory disease trait. In fact, out of 6 rat lines transgenic for HLA-B27 and h$\beta_2$m which have been developed to date by the inventors, two independent lines have demonstrated the ability to spontaneously develop an inflammatory disease trait. Thus, one will generally desire to generate at least 8 or so lines to be ensured that at least one of the resultant lines will exhibit the desired trait.

It has been observed by the inventors, in the case of transgenic rats incorporating HLA-B27, that those lines which exhibit the spontaneous inflammatory disease trait typically have incorporated a higher copy number of the selected transgene as compared to those transgenic rats with lines which do not exhibit such a trait. While it is not clear whether there is a direct correlation between copy number and propensity to spontaneously develop the trait, the correlation has been observed in these two cases and may be important. Therefore, one may desire to identify and select transgenic animals which have a relatively high copy number of the selected transgene incorporated into its genome, such as at least 20 copies, 30 copies, or 50 copies or even more of the selected transgene or transgenes.

The present invention also contemplates the introduction of class II major histocompatibility genes, such as those encoding the alloantigen HLA-DR4, whose expression product is associated with a propensity to develop rheumatoid arthritis. As noted above, while at least eight DR4 subtypes are now known, the Dw4 subtype has been the most closely associated with the development of rheumatic arthritis disease, and therefore should be considered preferred for practicing these aspects of the present invention.

Where one contemplates employing a class II MHC gene, it should be emphasized that the class II molecules are comprised of an alpha chain and a beta chain. DR molecules include an alpha chain which generally shows little variation among different individuals, and is encoded by the DRA locus. It is the beta chain that determines the specific allele of the DR molecule. The DR4 allospecificity is encoded in the beta chain locus termed DRB1 (Bodmer et al., 1990).

While the invention is directed in preferred embodiments to the generation of transgenic rats, and in particular, to transgenic rats having the propensity to spontaneously develop an inflammatory disease trait, it is believed that other non-human mammals will similarly exhibit such traits upon introduction of an appropriate transgene as set forth herein. While it is true that mice do not exhibit this ability, now that the phenomenon has been successfully demonstrated in rats, there is no reason why other non-human mammals, such as cows, pigs, rabbits, guinea pigs, sheep, hamsters, or even goats, could not be employed in this regard. This proposition is, of course, based on the observation that the mouse system has, for one reason or another, been an inappropriate system for generation of such an animal model of human disease.

In other aspects, the present invention concerns the general methodology for preparation of transgenic rat lines. These methods generally include first preparing a group of transgenic rats having incorporated into their genome at least one selected transgene, selecting at least one founder from said group of transgenic rats and breeding the founder or founders to establish at least one line of transgenic rats having the selected transgene incorporated into their genome.

The initial group of transgenic rats are generally prepared by introduction of DNA which includes the selected transgene into germ cells of the rat (typically fertilized eggs), which germ cells are then employed to generate the complete animal. Introduction of the DNA into the germ cells is most conveniently achieved by a technique known as microinjection wherein a solution containing DNA is introduced through the aid of a microscope and a microinjector pipet which deposits intact DNA into one of the two pronuclei. However, the inventors contemplate that other techniques may be employed for introduction of the DNA into the genome, including in vitro fertilization using sperm as a carrier of exogenous DNA, electroporation or transfection into a rat embryonic stem cell line and introduction of these cells into a rat blastocyst.

A particularly preferred method for preparing transgenic rats includes subjecting a female to hormonal conditions effective to promote superovulation, followed by fertilizing eggs of the superovulated female, and introducing the selected transgene into the fertilized eggs. In this embodiment, the fertilized eggs having the selected transgene are transferred into a pseudopregnant female rat, and brought to term. In that rats have traditionally been found to be difficult to effect superovulation, one will typically desire to employ the technique developed by Armstrong, et al., 1988, wherein immature rats are superovulated by a continuous infusion of follicle stimulating hormone, such as Folltropin® (Vetrepharm Inc., London, Ontario, Canada).

After superovulation is effected and the females are bred, the resultant eggs are collected (by flushing from the oviduct). While the presently preferred method for fertilizing the eggs is by breeding the female with a fertile male, superovulated eggs could be fertilized by artificial insemination of the female, or after removal, by in vitro fertilization.

After fertilization, the selected transgene is introduced into the fertilized eggs by a convenient method, for example, microinjection. (Note that it is even possible to introduce the DNA prior to fertilization.)

The next step, wherein fertilized eggs having the selected transgene are transferred into a pseudopregnant female, can be accomplished using techniques known in the art, for example, the techniques which are typically employed in connection with transgenic mice. (See e.g., Brinster, et al. 1985).

Once the fetuses in the pseudopregnant female have been brought to term, a founder animal is identified by standard techniques of hybridization of transgene DNA to genomic DNA from weanling offspring. The word "founder" is intended to refer to a transgenic animal which develops from the microinjected egg. The founders are tested for expression of a functional gene by any suitable assay of the gene product. Typically, cells obtained from the founders, such as white cells (leukocytes), are tested by immunofluorescence and flow cytometry with a test antibody against the gene product. Founders that express the gene, particularly those that express the gene at levels and with a tissue distribution that is comparable to that found for selected genes in general, are then bred to establish a line or lines of transgenic rats which have a selected transgene incorporated into their genomes.

The inventors contemplate that the foregoing technique can successfully be employed to develop rat lines having any of a number of genes, DNA segments or transgenically derived traits introduced into their genomes. As used herein, the term "line" is intended to refer to animals that are direct descendants of one founder and bearing one transgene locus stably integrated into their germline. Furthermore, it is contemplated that inbred lines can be developed from such lines wherein the rats that are used for microinjection are members of established inbred strains. As used herein, the term "inbred line" is intended to refer to genetically identical at all endogenous loci. Inbred lines may have particular advantages, for example, including reproducibility from one animal to the next, ability to transfer cells or tissue among animals, and the ability to carry out defined genetic studies to identify the role of endogenous genes.

A. The HLA-B*2705 gene (clone pE.1-B27) was contained on a 6.5 kb Eco R1 fragment. Exons are indicated by boxes and fragments labeled A and B, respectively, were used for dot-blot hybridization of genomic DNA. Probe C, from 3" untranslated region, was used for Northern hybridization.

B. The human $\beta_2$m gene (clone p$\beta_2$m-13) was contained on a 15 kb Sal I—Pvu I fragment. Exons are indicated by boxes. The insert contained ~100 bp of the vector pEMBL9, indicated by the open box at the 3' end. The 3.7 kb Bgl II fragment labeled D was used for both dot-blot hybridization of genomic DNA and for Northern hybridization.

FIG. 3. Comparison of Cell Surface Expression of HLA-B27, h$\beta_2$m, and the Endogenous RT1 Class I MHC Molecules in 21-4H, 21- 4L, and Nontransgenic Rats. Peripheral blood mononuclear cells were incubated with saturating concentrations of monoclonal antibodies and fluorescein-labeled second antibodies and then analyzed by flow cytometry, as described under Experimental Procedures. The results demonstrate that cell surface expression of both transgenes was at least as high in the clinically normal 21-4L line as in the disease-prone 21-4H line, and that endogenous RT1 expression appeared lower in the transgenic rats than in the nontransgenic control.

Source of cell populations:

(a) nontransgenic LEW stained with negative control antibody (panels A, B, C).

(b) 21-4H.

(c) 21-4L.

(d) nontransgenic LEW stained with anti-RT1 antibody (panel C).

Monoclonal antibodies:
(A) anti-HLA-B27 (B. 1.23.2 ).
(B) anti-h$\beta_2$m (BBM. 1).
(C) anti-RT1 class I (OX18).

Figure 4:
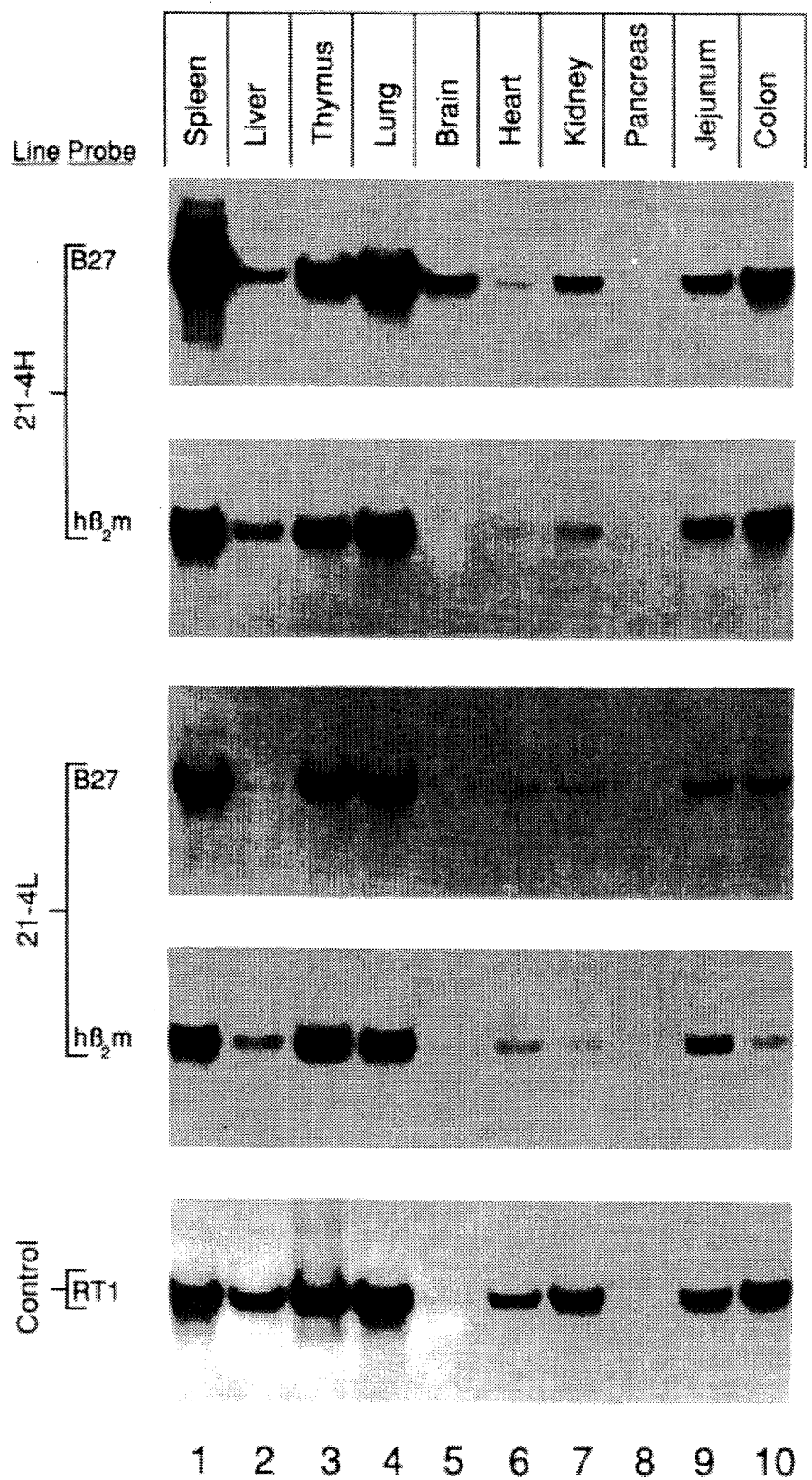

FIG. 4. Northern Blot Analysis of HLA-B27, h$\beta_2$m, and RT1 mRNA: Tissue Survey Total cellular RNA from tissues of (12) week old male 21-4H, 21-4L, and nontransgenic control rats were subjected to denaturing agarose gel electrophoresis (10 µg per lane), transferred to nylon membranes, and hybridized to $^{32}$P-labeled probes. Membranes were exposed to XAR-5 film at −70° with intensifying screens for 2 to 26 hours.

Figure 5A:
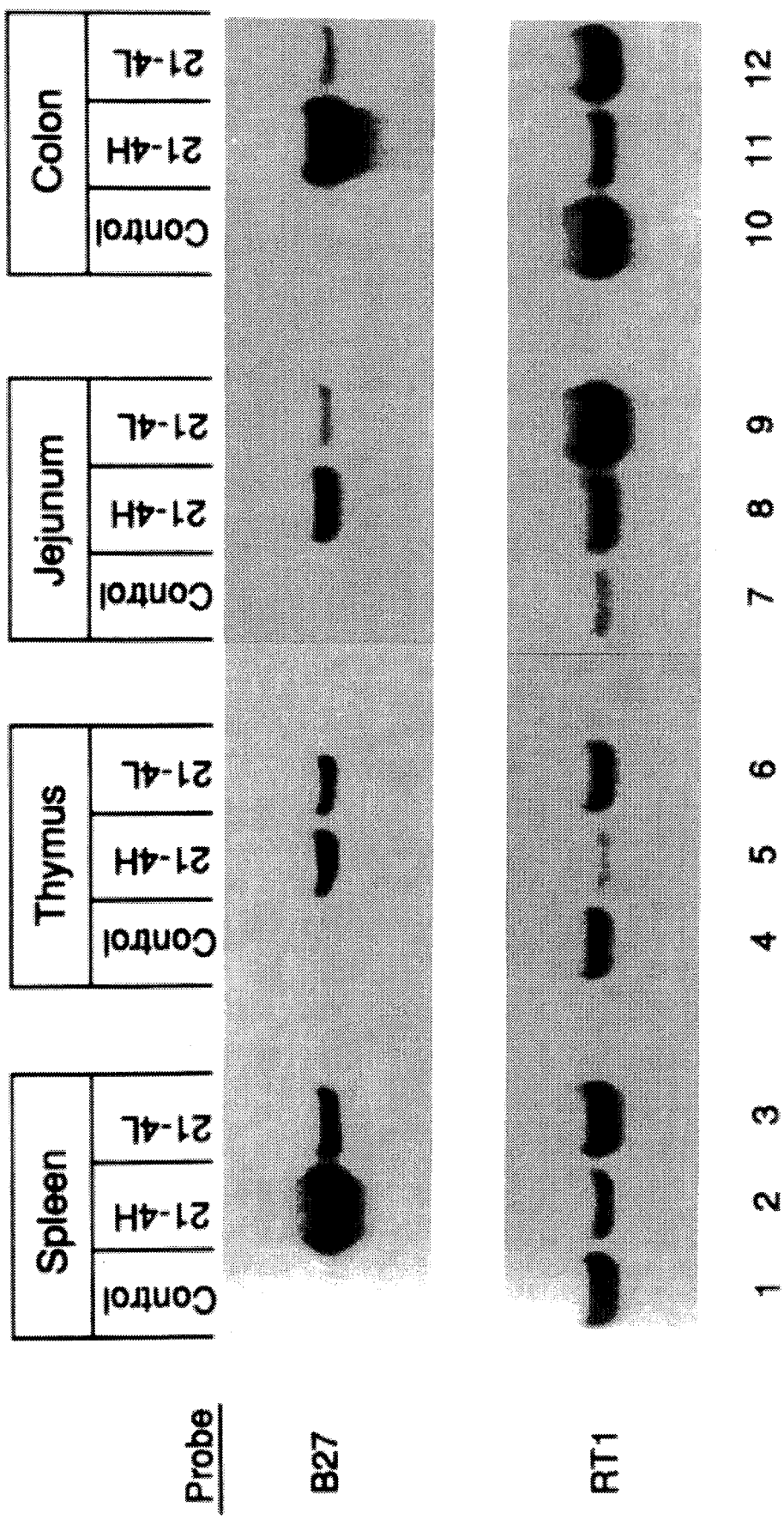
Figure 5B:
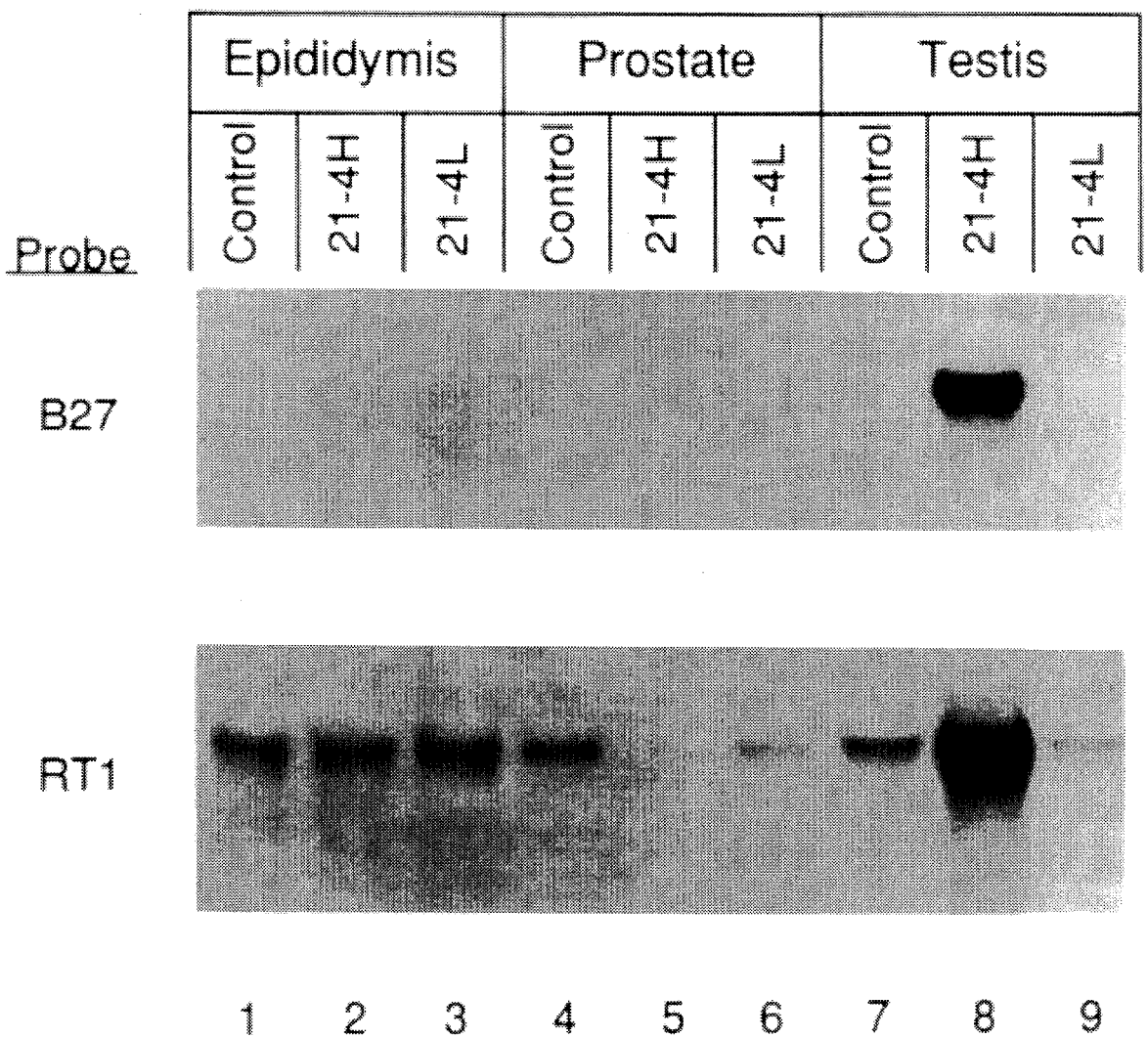

FIG. 5. Northern Blot Analysis of HLA-B27 and RT1 mRNA: Comparative Analysis of Seven Tissues.
  A. Tissue sources and methods were the same as described in FIG. 4. Membranes were exposed one to eight hours.
  B. Tissue sources were the same as described in FIG. 4. Five µg of total cellular RNA were added per lane. Prostatic tissue in the 21-4H animal was difficult to identify because of severe atrophy of all the accessory reproductive organs. The B27 probed membrane was exposed for one hour. A 10 hour exposure showed B27 transcripts in 21-4H epididymis. The RT1 probed membrane was exposed for 5 hours.

In the current model of class I MHC function, peptides, largely derived from intracellular protein synthesis, bind to the binding cleft of class I MHC molecules in the endoplasmic reticulum and are transported as a complex to the cell surface. The amino acids of the polymorphic regions of the $\alpha_1$ and $\alpha_2$ domains of class I MHC molecules are primarily responsible for their capacity to bind different peptides. After reaching the cell surface, endogenously synthesized peptide bound in the peptide-binding cleft is presented to CD8+T-lymphocytes expressing specific, clonally-distributed $\alpha$, $\beta$ antigen receptors capable of recognizing the combination of polymorphic MHC molecule plus peptide.

Examination of HIA-B gene products that react with conventional B27 typing alloantisera has identified six subtypes. These have been sequenced at the protein level and designated by the World Health Organization HLA Nomenclature Committee as B*2701, B*2702, B*2703, B*2704, B*2705, and B*2706, in order of the most acidic to most basic bands produced on isoelectric focusing gels (Bodmer et al. 1990; Lopez de Castro 1989). B*2701 has the highest isoelectric point and B*2706 has the lowest. The amino acids that vary among these different subtypes are shown in Table 1. B*2705 is the predominant subtype in all populations, although considerably less so in Orientals that in Caucasians. The B27 alleles are thought to have arisen from a single primordial gene.

TABLE 1

Nomenclature and amino acid differences of the HLA-B-27 subtypes

| New allele designation | Previous equivalents | Amino Acid positions* | | | | | | | |
|---|---|---|---|---|---|---|---|---|---|
| | | $\alpha_1$ domain | | | | | $\alpha_2$ Domain | | |
| | | 59 | 74 | 77 | 80 | 81 | 114 | 116 | 152 |
| B*2701 | 27f | Tyr | Tyr | Asn | Thr | Ala | His | Asp | Val |
| B*2702 | 27.2,27K,27e | — | Asp | — | Ile | — | — | — | — |
| B*2703 | 27J,27d | His | Asp | — | — | Leu | — | — | — |
| B*2704 | 27.3,27C,27b | — | Asp | Ser | — | Leu | — | — | Glu |
| B*2705 | 27.1,27W,27a | — | Asp | Asp | — | Leu | — | — | — |
| B*2706 | 27.427D | — | Asp | Ser | — | Leu | Asp | Tyr | Glu |

*Dashes indicate identity with B*2701.
Adapted from Khan, 1988; Rojo et al.., J Immunol 1987, 139:831–836; Choo et al., Immunogenics 1986, 23:29; Breur-Vrisendorp et al., Hum Immunol 1986, 16:163–168; Albert, Antigens 1988, 32:177–187.

DETAILED DESCRIPTION OF THE PREFERRED EMBODIMENTS

A. Structure of HLA-B27

HLA-B27 is a serologically defined allele of the HLA-B locus, one of the three classical HLA loci encoding class I major histocompatibility (MHC) gene products (HLA-A, B and C), which are 44 kDa glycoprotein molecules expressed on cell surfaces in noncovalent association with $\beta_2$-microglobulin $\beta_2$-m). The three-dimensional structure of two HLA class I molecules, HLA-A2 and HLA-Aw68, has been determined by x-ray crystallography (Bjorkman et al. 1987a; Bjorkman et al. 1987b; Garrett et al. 1989). The $\alpha_1$ and $\alpha_2$ domains are folded into peptide-binding cleft, with helical regions from each domain creating the two walls and anti-parallel $\beta$-pleated sheets from these two domains forming the floor. Most of the polymorphic amino acid residues in class I molecules are clustered along this cleft, projecting into it either from the two alpha-helices or from the floor of the $\beta$-pleated sheet. Adjacent to the $\alpha_1$-helix, pockets project from the cleft under the $\alpha$-helix that interact with amino acid residues outside the cleft (Garrett et al. 1989).

Figure 1:
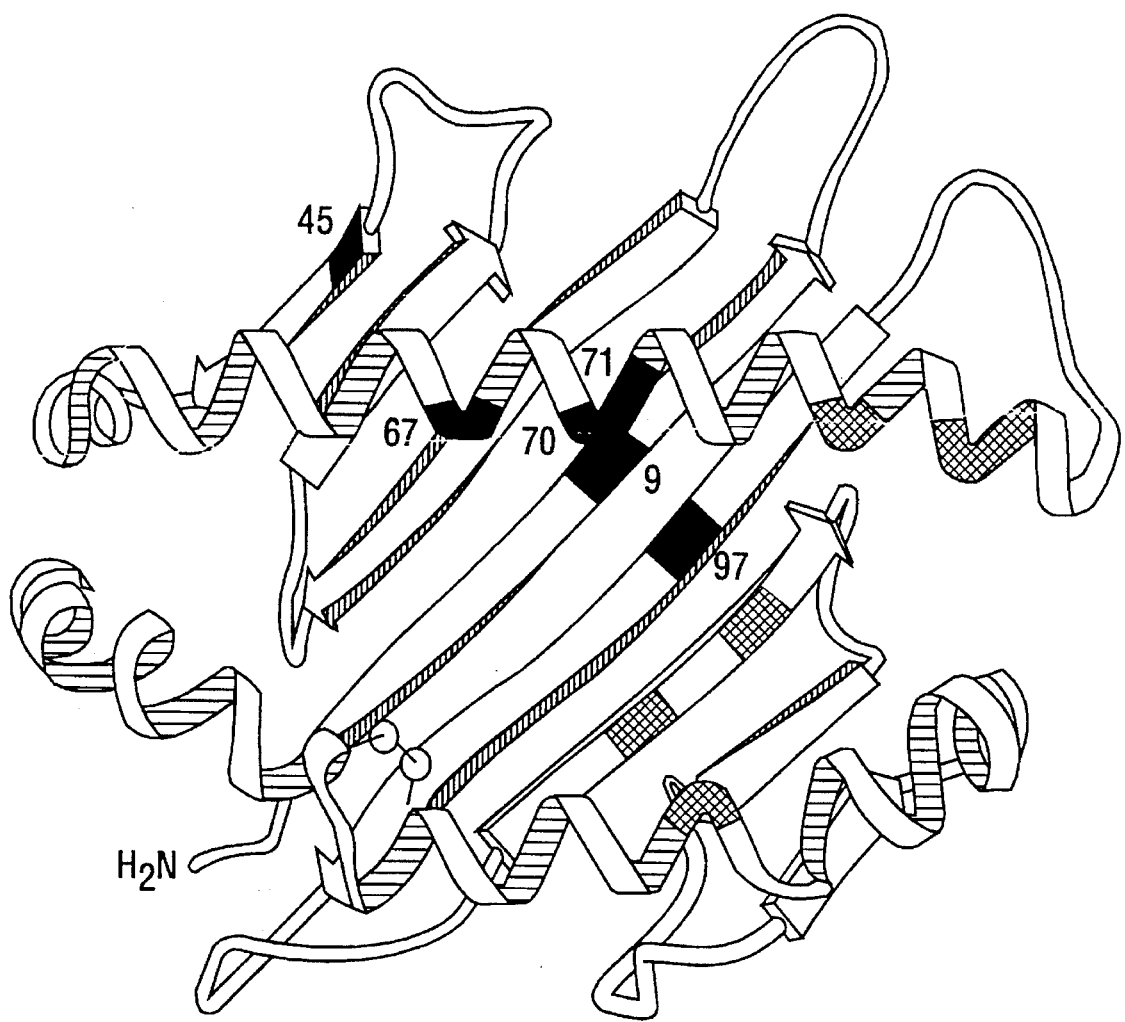
FIG. 1. Situation of conserved (solid) and polymorphic (stippled) residues of the four ankylosing spondylitis-associated HLA-B27 subtypes (HLA-B* 2702, -04, -05, -06), as modeled on the three-dimensional structure of HLA-A2 (Bjorkman et al., Nature 1987, 329: 506–512). (From Benjamin and Barham, Immunol. Today 1990, 11: 137–142.)

Superimposition of the primary structure of B27 on the crystallographic class I MHC model is shown in FIG. 1. Comparison of the B27 subtypes with other HLA class I sequences (Parham et al. 1988) indicates two amino acid residues unique to all of the B27 subtypes, Lys at 70 and Asn at 97, which are located near each other in the three-dimensional structure of the molecule, both pointing into the peptide-binding cleft (FIG. 1). Benjamin and Parham (1990) have recently pointed out that the consensus B27 sequence shares a cluster of six amino acids within the peptide-binding cleft; these include the two B27-unique residues Lys70 and Asn97, as well as His9, Glu45, Cys67, and Ala71 (FIG. 1). It seems reasonable to include Ala69 to this cluster as well. No other known class I HLA sequence shares more than two of these residues with B27. This part of the B27 molecule therefore appears to be a prime candidate for participation in the pathogenesis of B27-associated disease, perhaps by binding a unique peptide or peptides that might initiate or propagate the disease.

The Cys67 residue is of particular interest because it is unpaired and thus presents a potentially reactive sulfhydryl group into the peptide binding cleft. Biochemical evidence has been obtained that the Cys67 residue expressed on cell surfaces bears a reactive sulfhydryl group (McLean et al. 1989). Although HLA-B14 and B65 also have a Cys residue at position 67, the environment surrounding position 67 in these molecules differs considerably from B27, lacking charged residues at 45, 63, and 70 (Parham et al. 1988). These changes would tend to make the Cys67 in B14 or B65 less available to disulfide formation with a peptide than is the case for B27. Position 67 of B27 is not only important because of its potential to bind peptides covalently, but also because it influences the conformation of the molecule; thus, substitution of Cys67 in B27 with other residues by site-directed mutagenesis and gene transfection alters the structure of B27 defined by several monoclonal antibodies (El-Zaatari et al. 1990; Taurog and El-Zaatari 1988).

An important question is whether B27-associated disease is associated preferentially with one or more of the B27 subtypes. In the case of AS, it has been reasonably well shown that there is no preferential association. Of the B27 subtypes, B*2701 and B*2703 have been found only in a few individuals (Choo et al. 1986), and thus have not been amendable to population studies. However, non-preferential association of AS with at least three of the other subtypes was shown in a study that did not distinguish between B*2704 and B*2706 (Breur-Vriesendorp et al. 1987). Therefore, it is not unlikely that AS is associated with each of the B27 alleles. Whether each of the B27 alleles is also associated with the other spondyloarthropathies is currently unknown, but appears to be a likely possibility.

B. Rheumatic Diseases Associated With HLA-B27 in Humans

A summary of the major disorders in which there is a significant association with B27 is presented in Table 2.

TABLE 2

Rheumatic Diseases Associated with HLA-B27

| Characteristic | Ankylosing spondylitis | Reactive arthritis | Juvenile spondylo-arthropathy | Psoriatic arthropathy | Enteropathic arthropathy |
|---|---|---|---|---|---|
| Sacroiliitis or spondylitis[b] | 100% | <50% | <50% | 20% | 10% |
| Peripheral arthritis[c] | 25% | 90% | 90% | 95% | 90% |
| Gastrointestinal inflammation | Common, usually asymptomatic | Common, often symptomatic | Not known | Uncommon | All |
| Skin and nail involvement | Rare | Most | Uncommon | All | Uncommon |
| Genitourinary involvement (males only) | Uncommon | Most | Uncommon | Uncommon | Rare |
| Eye involvement | 25% | Common | Common | Occasional | Occasional |
| Cardiac involvement | <5% | 5–10% | Not known, probably rare | Rare | Rare |
| Usual age of onset (years) | 18–40 | 18–45 | 7–18 | 20–50 | 15–50 |
| Sex prevalence | Males 3:1 | Males 3:1[e] | Males 10:1 | Equal | Equal |
| Type of onset | Gradual | Acute | Variable | Variable | Gradual |
| Role of infectious agents | Unknown | Definite Trigger | Unknown | Unknown | Unknown |
| Prevalence of HLA-B27[f] | >90% | 60–80% | 80% | 50%[g] | 50–75%[g] |

[a]Includes Reiter's syndrome, classically defined as the triad of arthritis, conjunctivitis, and urethritis.
[b]Inflammation in the spine or sacroiliac joints.
[c]Inflammation in joints of the extremities.
[d]Predominantly conjunctivitis in reactive arthritis, iritis with the other disorders.
[e]Male:female ratio is 10:1 if venereally acquired, 1:1 for enteropathically acquired.
[f]Caucasians of northern European extraction only. General prevalence in this population is 6–8%. Some variation seen in other populations, but the basic associations with HLA-B27 are seen worldwide.
[g]Frequency elevated only in those with spondylitis or sacroiliitis.
(Adapted from Calin 1984; Tiwari and Terasaki 1985; Khan and van der Linden 1990; Taurog and Lipsky 1990)

C. The Inflammatory Disease of the 21-4H and 33-3 Transgenic Rats: Comparison with B27-Associated Disease in Humans B27-associated disorders in humans encompass a spectrum of inflammatory diseases affecting predominantly the peripheral and axial musculoskeletal system, gastrointestinal tract, genital tract, integument, and eye (Table 2). Less common involvement of heart and nervous system and rare involvement of lung are also observed in these disorders (Bulkley and Roberts 1973; Good 1974; Taurog and Lipsky 1990). The spontaneously arising disease in B27/h$\beta_2$m transgenic rats shows a striking clinical and histologic similarity to B27-associated disease in humans, with inflammatory lesions of peripheral and axial joints, gut, male genital tract, nails, skin, and heart. The close resemblance of the findings in the transgenic rats to B27-associated disease in humans strongly supports the conclusion that the B27 molecule itself participates in the pathogenesis of the various lesions found in different organ systems in the spondyloarthropathies.

The most prevalent site of inflammation in the transgenic rats appears to be the gastrointestinal tract. Greater than 90% of the 21-4H and 33-3 rats under observation for at least 6 months developed overt diarrhea. These findings suggest that the events initiating the disease process may occur in the gastrointestinal tract, and that further investigation of the intestinal immunophysiology and immunopathology of the transgenic animals may provide some insight into the role of the B27 molecule in these events.

Numerous observations in humans support a causal link between factors in the gut and inflammatory joint disease. Peripheral and axial arthritis are common accompaniments of chronic inflammatory bowel disease even in the absence of B27 (Table 2), and recent evidence suggests that milder degrees of gastrointestinal inflammation are closely correlated with the occurrence of B27-associated joint disease in individuals without bowel symptoms. Histologic examination of endoscopically obtained biopsies in a large series of patients with reactive arthritis or ankylosing spondylitis indicated that over 60% had asymptomatic inflammatory lesions of the terminal ileum or colon (Cuvelier et al. 1987). Whether patients with B27-associated disease develop inflammatory lesions in the more proximal small intestine or stomach that might resemble those seen in the 21-4H rats is not known.

Although gastrointestinal inflammation in the transgenic rats was present equally in both sexes, arthritis occurs more frequently in males. This closely followed the pattern in humans, in whom males with ankylosing spondylitis, juvenile onset spondyloarthropathy, or reactive arthritis following genital infection outnumber females 3 to 10 fold. The prevalence of subclinical gastrointestinal inflammation in B27 individuals without rheumatic disease, either male or female, is not known. Both peripheral and axial arthritis occurred in the 21-4H rats. Peripheral arthritis was also seen in 33-3 rats, whereas axial arthritis has not yet been seen in this line. Clinically, the peripheral arthritis resembles that seen in other experimental models of arthritis in rats, such as those induced by complete Freund's adjuvant or streptococcal cell walls, with swelling and erythema of the proximal hind limb being the predominant lesion. Histologically, the involved joints show lesions typical of experimental arthritis in rats, as well as B27-associated peripheral arthritis in humans, with synovial hyperplasia, inflammatory cell infiltration, pannus formation, and destruction of articular cartilage and bone (Greenwald and Diamond 1988; Taurog et al. 1988b).

Axial arthritis, with inflammatory cell infiltration and periosteal reaction at the margins of the intervertebral discs, has been seen histologically in the tails of 21-4H rats. This appears to be the same pathologic process that leads to the vertebral changes in ankylosing spondylitis, although histologic comparison of this lesion with human spondylitis is made difficult by the paucity of descriptions of early lesions in humans (Ball 1971; Eulderink 1990). More generally, the vertebral lesion in the 21-4H rats also closely resembles enthesitis, inflammation at ligamentous attachments to bone, that is a pathologic hallmark of the B27-associated diseases in humans (Ball 1971).

Dramatic psoriasiform skin and nail lesions developed in the 21-4H rats. These lesions show an extraordinary histologic resemblance to psoriatic lesions in humans, representing the first reported instance of psoriatic lesions in a laboratory animal. Although in most patients with psoriasis vulgaris there is no association with HLA-B27, lesions termed keratoderma blenorrhagicum that are histologically indistinguishable from the psoriatic variant pustular psoriasis are commonly found in B27-associated reactive arthritis (Good 1974; Keat 1983). Furthermore, typical psoriasis vulgaris occasionally supervenes in patients initially presenting with reactive arthritis, who are predominantly B27+. Finally, a common pathogenetic mechanism between psoriasis vulgaris and B27-associated disease is suggested by the recent observation that both psoriasis vulgaris and the skin lesions of Reiter's syndrome appear to be significantly exacerbated in patients with these conditions who have co-existent infection with the human immunodeficiency virus HIV-1 (Duvic et al. 1987).

Another striking lesion in the 21-4H rats was orchitis, which was found in virtually all of the males, invariably in association with epididymitis. In humans, urogenital inflammation is prevalent in B27-associated diseases. Although urethritis in males with reactive arthritis is a common finding even in the absence of known urethral infection, prostatitis and epididymitis in males, cervicitis in females, and cystitis in both sexes have been described (Yli-Kerttula 1984). Although there have been no reports of histologically confirmed orchitis associated with HLA-B27 or with B27-associated syndromes, clinical descriptions suggestive of orchitis have been reported (Montanaro and Bennett 1984). It is thus not altogether unlikely that the inflammatory process induced by B27 in the 21-4H rat testis has a milder human counterpart. In the 33-3 rat, the predominant genital lesion appeared to be epididymitis rather than orchitis.

Inflammatory disease involving the root of the aortic valve and myocardium is found in the 21-4H rats. Both aortic insufficiency and cardiac conduction disturbances are well-documented complications of ankylosing spondylitis and reactive arthritis (Bergfeldt et al. 1988; Bulkley and Roberts 1973; Good 1974). Moreover, primary myocardial disease may also be relatively prevalent in ankylosing spondylitis (Brewerton et al. 1987). The cardiac pathology of the 21-4H rats, like the lesions in the peripheral and axial joints, gastrointestinal tract, skin, and male genital tract, thus appears to be a direct counterpart of a pathologic process in B27-associated human disease.

In comparing the pathologic lesions identified in the B27 transgenic rats with B27-associated disease in humans, only the neurologic disease in the 21-4H LEW line seemed to represent a significant anomaly. Occasional cases of either central or peripheral neurologic disease have been reported in association B27-associated reactive arthritis (Good 1974; Montanaro and Bennett 1984; Taurog and Moore 1986), but none of these has been characterized histologically, nor do their clinical descriptions resemble the findings in the 21-4H rats. As mentioned under Example I, the neurologic lesions in the 21-4H rats appear to be temporally and histologically unrelated to the inflammatory disease seen in other organs. Although the possibility cannot be excluded that the neurologic disturbance contributes indirectly to the inflammatory lesions, for example by disruption of the normal innervation of lymphoid tissue or gut (Anderson 1990), the absence of neurologic disease in the 33-3 line, a second transgenic line exhibiting spontaneously occurring B27-associated disease, suggests that the neurologic disease in the 21-4H line is not a necessary part of the inflammatory process in other organ systems, but perhaps a result of a dominant insertional mutation.

D. The Inflammatory Disease of B27/h$\beta_2$m Transgenic Rats: Possible Mechanisms It is unclear why overt inflammatory disease developed in only two of the seven transgenic rat lines, 21-4H and 33-3. It is unlikely that differences in postconceptional environment play a significant role in determining the phenotypes of the different transgenic lines, since segregation of the diseased phenotype with the 21-4H locus was uniformly observed in litters containing both 21-4H and 21-4L offspring. Insertional mutation appears unlikely as an explanation, since two independent transgenic lines developed a similar disease. Nor has evidence been obtained for differences in B27 function, since the 21-4H and 21L lines comparably stimulated immune recognition of B27 by cytolytic T cells. The variation among transgenic rat lines most likely can be ascribed to either quantitative or qualitative differences in the expression of the transgenes or to differing effects of the transgene on the host genome.

Several lines of evidence have suggested that interactions between B27 and bacteria products are involved in the pathogenesis of the spondyloarthropathies (Yu et al. 1989). Although the disease in the transgenic rats arose spontaneously in the apparent absence of infection by pathogens, the possibility must be considered that the pathogenesis involves interactions between B27 and commensal organisms such as the intestinal flora or infectious agents not detected by routine seologic surveillance of the animal colony. Studies in which the transgenic rats are maintained germ-free will be important in exploring this issue.

Despite extensive investigation of the structure and function of class I MHC genes in general and HLA-B27 in particular, it has so far not been possible to identify the molecular mechanism of the association of B27 with human disease. However, given the close resemblance of the spontaneous disease of the 21-4H and 33-3 lines to B27-associated human disorders, a detailed cellular and molecular analysis of the B27/h$\beta_2$m transgenic rats should enhance our understanding of the role of HLA-B27 in causing disease. It may also contribute to a broader understanding of the function of class I MHC molecules.

The following examples illustrate preferred embodiments of the present invention in terms of laboratory practices found by the present inventors to work well in the practice of the invention. However, in light of this disclosure, those of skill in the art will appreciate that numerous alternatives may be employed without departing from the spirit and scope of the invention. Therefore, the present invention is not intended to be limited to the specific methodology set forth hereinbelow.

EXAMPLE I

Transgenic Rats Expressing HLA-B27 and Human $\beta_2$-Microglobulin: Spontaneous Inflammatory Disease in Multiple Organ Systems in an Animal Model of HLA-Associated Human Disease 1. Methodology
   a. Animals Specific patbogen-free inbred Lewis/CrlBR (LEW) and Fischer F-344/CrlBR (F344) rats, and outbred Sprague-Dawley rats, were purchased from Charles River, Boston, Mass. Hybrid mice of the transgenic line 56-3 (Taurog et al. 1990), which express high levels of both B27 and h$\beta_2$m on lymphoid cell surfaces, were bred in our animal colony. Animals were maintained in accordance with institutional guidelines.

b. Generation and Identification of Transgenic Rats

Immature LEW or F344 female rats were superovulated according to the method of Armstrong & Opavsky (1988) as follows: in the morning, two days prior to eliciting superovulation, two mls of diluent was added to a vial of Folltropin® (FSH) and allowed to dissolve for about 30 minutes. (The diluent comes packaged with the Folltropin®, which may be obtained from Vetrepharm, Inc., London, Ontario). Mini-pumps were then loaded as described in the product literature (Alza Corporation, Palo Alto, Calif.), and installed subsequently between the scapulae. Forty eight hours after the time which the pumps were installed, the females were injected with 10 IU hCG ip. and placed with stud males. Typically, one female was placed with two males. On the morning of the next day, a check was made for copulatory plugs or vaginal smears were performed to check for sperm in the lavage. That afternoon, fertilized one-cell eggs were flushed from the oviducts of females exhibiting either a vaginal plug or sperm in vaginal lavage fluid, and eggs were held in Brinster's medium for two hours or less before microinjection.

Note that one may desire to vary the time of flushing in order to optimize for the best time to visualize pronuclei. Typically, immature female rats weighing 60–65 g are employed. Moreover, since the pumps are typically good for seven days, they can be removed from one group of females and reinstalled immediately into a new group.

Microinjection of eggs and transfer to day 1 pseudopregnant Sprague-Dawley females were carried out essentially as described for mice (Brinster et al. 1985). Briefly, cumulus cells were removed from the eggs with hyaluronidase at about 300 units/mi. Then, the eggs were washed free of debris and enzyme. For injection, the eggs were transferred to a depression slide in Brinster's medium modified by substitution of 25 mM Hepes buffer (pH 7.4) for the bicarbonate and inclusion of cytochalasin B (5 µg/ml). The medium was overlaid with silicone oil (Dow Corning 200 Fluid, 50 centistokes). Eggs were sequentially held in place by a blunt pipet (outside diameter about 100p) while the tip of the injector pipet was inserted through the zona pellucida and vitellus and into one of the pronuclei. The DNA solution in the injector pipet was slowly discharged by using a 100-µl Hamilton syringe connected to a micrometer. The injector pipet was filled with silicone oil except for the DNA solution. After injection, the eggs were washed free of cytochalasin B and transferred to the oviducts of pseudopregnant, Sprague-Dawley female rats.

Two genomic clones were used for microinjection of fertilized rat eggs (FIG. 2). The HLA-B27 gene encoding the HLA-B*2705 subtype (Bodmer et al. 1990) was contained on a 6.5 kb Eco RI fragment (clone pE.1-B27, Taurog and El-Zaatari 1988) and the human $\beta_2$m gene was contained on a 15 kb Sal I - Pvu I fragment (clone p$\beta$2m-13, Güssow et al. 1987, the gift of Dr. H. L. Ploegh, Amsterdam, The Netherlands). Each insert was separated from plasmid DNA by agarose gel electrophoresis and isolated by perchlorate elution (Chen and Thomas 1980). The solution used for microinjection contained both fragments, each at about 1.5 ng/µl.

Identification and quantitation of transgenes was determined in the founder animals and their progeny by dot-blot hybridization of genomic DNA isolated from tail biopsies, as previously described (Brinster et al. 1985). Genomic DNA was analyzed by hybridization with 5' and 3' flanking probes for the HLA-B locus, as previously described (probes A and C in FIG. 2A, Taurog et al. 1988a), and with a 3.7 kb Bgl II fragment containing exons 2 and 3 of the h$\beta_2$m gene (probe D in FIG. 2B).

c. RNA Analysis by Northern Blot Hybridization

Northern blot hybridization was carried out as described (Maika et al. 1990). Briefly, total cellular RNA was extracted from tissues by the guanadinium isothiocyanate-CsCl procedure, separated on glyoxal agarose gels, and blotted onto nylon membranes. HLA-B27 mRNA was detected with the 350 bp HLA-B 3' untranslated region probe pHLA-1.1

Figure 2A:
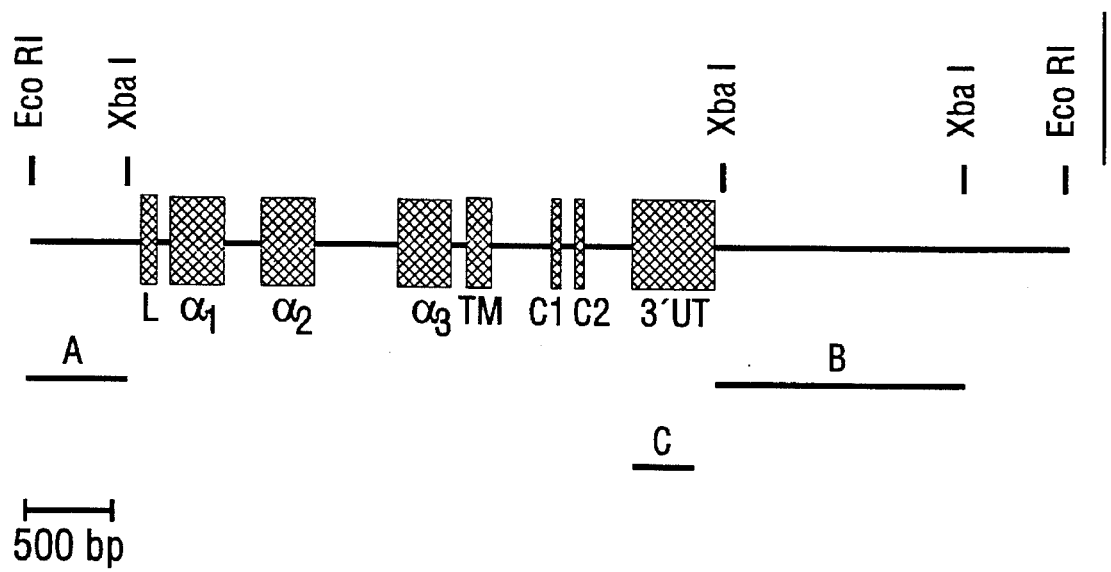
FIG. 2. Genes used for Microinjection of fertilized rat eggs.
Figure 2B:
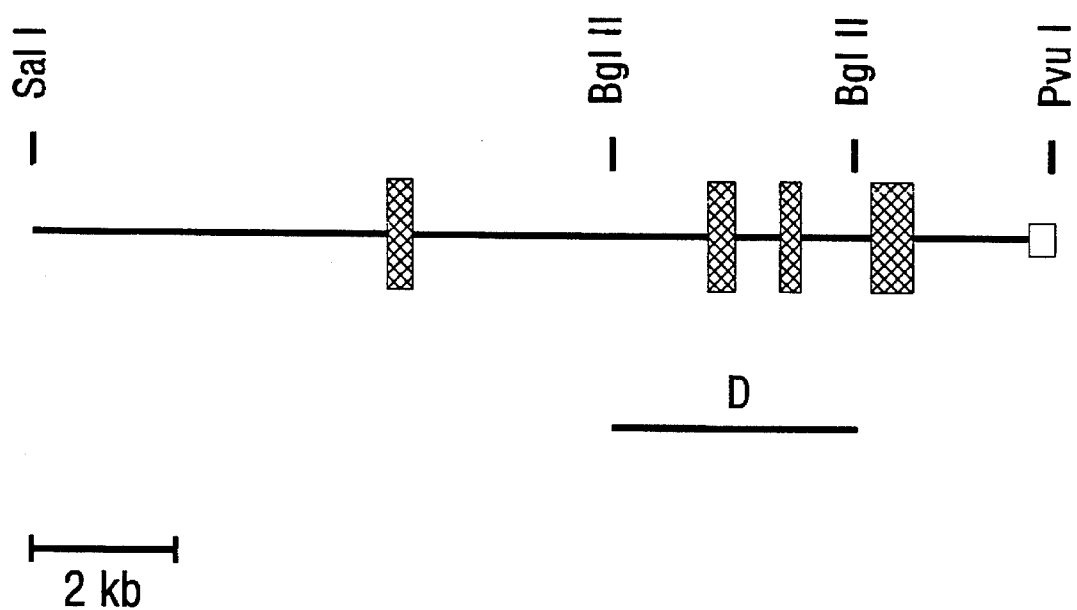

(probe B in FIG. 2A, Koller et al. 1984), and h$\beta_2$m mRNA was detected with the same 3.7 kb Bgl II fragment used to detect h$\beta_2$m genomic DNA (probe D in FIG. 2B). RT1 class I mRNA was detected with a 447 bp Pvu II-Hind III fragment containing the 3'-untranslated region of the RT1.A$^a$ gene pBS3.3/1 (Rada et al. 1990, the gift of Dr. J. C. Howard, Cambridge, U. K.) All stringency washes were carried out in 0.1X SSC/0.5% SDS at 65° C.

d. Monoclonal Antibodies, Indirect Immunofluorescence and Flow Cytometry

The following murine monoclonal antibodies were used: B.1.23.2, IgG$_{2a}$, binding a monomorphic determinant shared by HLAB and -C molecules (Rebai and Malissen 1983); BBM.1, IgG$_{2b}$, binding human $\beta_2$-microglobulin (Brodsky et al. 1979); and OX18, IgG$_1$, binding a monomorphic rat RT1 class I antigen (Fukumoto et al. 1982). P1.17, an IgG$_{2a}$ myeloma, served as a negative control.

Indirect immunofluorescence was carried out as previously described (Taurog and El-Zaatari 1988; Taurog et al. 1988a). Briefly, Ficoll-Hypaque purified peripheral blood mononuclear cells were incubated with saturating concentrations of each monoclonal antibody, washed, then incubated with fluorescein-conjugated F(ab')$_2$ fragments of goat-anti-mouse Fc antibodies (Cappel Inc., Malvern, Pa.). After washing, the cells were fixed in 1% paraformaldehyde before analysis on a FACScan flow cytometer (Becton Dickinson, Mountain View, Calif.). Viable lymphocytes were selected for analysis by gating of forward and 90° light scatter.

e. Generation and Analysis of Cytolytic T Cells

Primary alloimmunization by skin grafting was carried out by the method of Peter and Feldman (1972). Seven days after graft placement, recipient spleen cells were used as effector cells in a 4–6 hr $^{51}$Cr release assay, as previously described (Taurog et al. 1988a). Two mouse L cell lines were used as target cells, one transfected with and expressing the h$\beta_2$m gene, the other transfected with and expressing both the HLA-B*2705 and h$\beta_2$m genes, as described by El-Zaatari et al. (1990).

f. Histology

Tissues were fixed in 10% neutral buffered formalin, embedded in paraffin, sectioned, and stained with hematoxylin and eosin. Joints were embedded and sectioned following fixation and decalcification for 4–6 weeks in 10% disodium EDTA, as previously described (Taurog et al. 1988b), or following decalcification in 10% formic acid. Eyes were embedded in methacrylate before sectioning and staining.

2. Results a. Integration of HLA-B27 and h$\beta_2$m Genes in Inbred Rats

Fertilized one-cell rat eggs were microinjected with a solution containing both DNA fragments shown in FIG. 2. The HLA-B27 gene encoding the HLA-B*2705 subtype was contained on a 6.5 kb Eco RI fragment that included 0.7 kb of 5' flanking sequence and 2.5 kb of 3' flanking sequence (FIG. 2A). The human $\beta_2$m gene was contained on a 15 kb Sal I - Pvu I fragment that included 5.2 kb of 5' flanking sequence and 1.9 kb of 3' flanking sequence (FIG. 2B). Identification and quantitation of transgenes in the founder animals and their progeny was determined by dot-blot hybridization of genomic DNA isolated from tail biopsies. Hybridization was carried out with 5' and 3' flanking probes for the HLA-B27 gene (probes A and C in FIG. 2A), and with a 3.7 kb Bgl II fragment containing exons 2 and 3 of the h$\beta_2$m gene (probe D in FIG. 2B).

Seven LEW and four F344 rats that developed from microinjected ova showed integration of the HLA-B27 and h$\beta_2$m, as assessed by indirect immunofluorescence of peripheral blood lymphocytes (PBL). One additional LEW rat showed integration and expression of the B27 gene alone. Table 3 summarizes the results of the microinjection experiments, and Table 4 identifies the individual lines which were developed along with the copy number and cell surface expression of HLA-B27 and h$\beta_2$m for each.

TABLE 3

Production of HLA-B27 and h$\beta_2$m Transgenic Rats

| | | | Founder | | | |
|---|---|---|---|---|---|---|
| | | | Integration[b] | | Expression[c] | |
| Strain | Eggs[a] | Pups | B27 | h$\beta_2$m | B27 | h$\beta_2$m |
| LEW | 348 | 23 | 8 | 7 | 5 | 4 |
| F344 | 329 | 24 | 4 | 4 | 1 | 1 |

[a]Number of eggs injected and transferred to pseudopregnant recipients.
[b]Transgenic animals were identified by dot blot analysis of DNA isolated from tails.
[c]Cell surface expression was assessed by indirect immunofluorescence and FACS analysis of peripheral blood lymphocytes.

TABLE 4

Copy Number and Cell Surface Expression of HLA-B27 and h$\beta_2$m in transgenic Rat Lines

| | Gene[a] (copy/cell) | | Cell Surface Expression[b] (relative MCF) | |
|---|---|---|---|---|
| Line | B27 | h$\beta_2$m | B27 | h$\beta_{2m}$ |
| 21-2 | 1 | 1 | 0.09 | 0.06 |
| 21-3 | 20 | 15 | 0.30 | 0.29 |
| 21-4L | 6 | 6 | 0.74 | 0.42 |
| 21-4H | 150 | 90 | 0.51 | 0.42 |
| 25.1 | 1 | 0 | 0.15 | 0.42 |
| 25-6 | 7 | 7 | 0.42 | 0.27 |
| 33-3 | 55 | 66 | 1.00 | 0.76 |

[a]Gene copy number was estimated by quantitative dot hybridization on DNA isolated from tails using probes specific for each transgene (See FIG. 2A).
[b]Mean channel fluorescence (MCF) with antibodies to HLA-B (B1.23.2) or h$\beta_2$m (BBM.1) of PBL from transgenic rats, relative to simultaneously determined MCF of PBL from the B27/h$\beta_2$m transgenic mouse line 56-3. All data from progeny of founders to eliminate influence of mosaicism.

All of the founder rats expressing the transgenes were subsequently shown to transmit the transgenes to their offspring. One of the six founders, 21-3, was found to be a mosaic, based on non-Mendelian rates of transmission and on enhanced cell surface expression in the offspring. Another founder, 21-4, a female, was shown to have two independently segregating loci of transgene integration, each locus carrying both transgenes. One line arising from this founder, inheriting a locus containing 150 copies of the B27 gene and 90 copies of the h$\beta_2$m gene, was termed 21-4H. The other line, inheriting a locus containing 6 copies of the B27 gene and 6 copies of the h$\beta_2$m gene, was termed 21-4L (Table 4).

b. Lymphocyte Cell Surface Expression of the HLA-B27 and h$\beta_2$m Transgene Products Expression of the transgene products was estimated by indirect immunofluorescence and flow cytometry of PBL stained with specific monoclonal antibodies. The relative expression of B27 and h$\beta_2$m in seven transgenic lines is shown in Table 4. To compensate for interexperiment variation, the mean channel fluorescence for each line with each antibody is expressed relative to that determined in the same experiment for PBL of the transgenic mouse line 56-3, which expresses high levels of both B27 and h$\beta_2$m on PBL surfaces. The highest expression of both gene products was found in the LEW lines 21-4H and 21-4L and the F344 line 33-3.

The patterns of cell surface expression of B27 and $h\beta_2m$ in the 21-4H and 21-4L lines are shown in FIG. 3, panels A and B. The binding of the endogenous rat class MHC I molecules (RT1) to the anti-RT1 antibody OX18 is shown in panel C for both transgenic lines and the nontransgenic control. The levels of expression of B27 and $h\beta_2m$ were comparable in the two transgenic lines (panels A and B), and in both lines the expression of the endogenous RT1 class I molecules appeared to be reduced in comparison with the nontransgenic control (panel C).

c. Immunologic Function of the HLA-B27 Transgene

To assess T cell recognition of the B27 transgene product as a class I MHC antigen, primary grafts of B27 transgenic LEW rat skin were placed on nontransgenic LEW rats, and spleen cells from the recipient rats were subsequently tested for B27-specific cytotoxicity. As shown in Table 5, spleen cells from nontransgenic LEW rats receiving grafts from either 21-4H or 21-4L donors showed significantly higher lytic activity against L cell targets transfected with the B27 gene than against otherwise identical targets lacking this gene. Lytic activity was also higher in recipients of transgenic grafts than in recipients of control nontransgenic syngeneic grafts. These results indicate that the B27 transgene product is recognized in a conventional manner by allogeneically primed cytolytic T cells.

TABLE 5

Cell-Mediated Cytotoxicity Against HLA-B27

| Effector Cells Donor | Effector Recipient | Target Ration | Target Cells $B27^+ h\beta_2m^+$ | $B27^- h\beta_2m^+$ |
|---|---|---|---|---|
| | | | % Cytotoxicity | |
| Experiment 1 | | | | |
| 21-4L | LEW | 100 | 34 | 15 |
| | | 50 | 38 | 8 |
| | | 20 | 36 | 3 |
| LEW | LEW | 100 | 19 | 13 |
| | | 50 | 14 | 7 |
| | | 20 | 5 | 1 |
| Experiment 2 | | | | |
| 21-4H | LEW | 100 | 18 | 7 |
| | | 50 | 8 | 4 |
| | | 20 | 3 | 2 |
| LEW | LEW | 100 | 3 | 3 |
| | | 50 | 1 | 2 |
| | | 20 | 0 | 1 |

Spleen cells from LEW rats grafted 7 days earlier with skin from either 21-4 transgenic or normal LEW donors were incubated at the indicated effector target ratios with $^{51}$Cr-labeled murine L cell targets expressing either $h\beta_2m$ alone or $h\beta_2m$ and HLA-B27. Incubation times = exp. 1, 6 hr., exp. 2, 4 hr. S. D. were $\leq$ 15% in exp. 1 and < 10% in exp. 2 d. Inflammatory Disease in the 21-4H Line: Clinical and Histologic Findings in a Cohort of 23 Rats 1. Gastrointestinal tract Overt disease appeared in all of the rats bearing the 21-4H transgene locus that survived past 10 weeks of age. This cohort consisted of 14 males and 9 females. The most common and persistent finding was diarrhea, manifested by frequent, voluminous, often watery stools. Diarrhea was observed in all 23 animals, with equal persistence and severity in the two sexes. Histologically, the gastrointestinal disease was manifested by chronic inflammation involving the stomach and small and large intestine. The distribution and severity of the lesions varied, the colon being the most consistently and prominently affected site. Less frequently, gastric lesions predominated. In all sites, the inflammatory cells consisted primarily of large and small lymphocytes, plasma cells, and smaller numbers of eosinophils. Although the inflammatory response remained primarily in the lamina propria, in the most severely affected regions it extended into the submucosa. Lymphocytes were commonly aggregated into small hyperplastic lymphoid foci, especially in the colon and ileum.

In the intestinal lesions, hyperplasia of crypt epithelial cells replaced mucus-secreting cells and increased the depth of the crypts. Hyperplastic crypt cells showed regenerative atypia and a marked increase in mitotic activity. Destruction of crypts and/or the formation of crypt abscesses was uncommon and seen only in the most inflamed areas.

The gastric lesions generally consisted of widely scattered inflammatory foci in the lamina propria and submucosa, but in more severe lesions inflammation was much more extensive, and inflammatory cells accumulated in ectatic glands. The proliferation of mucus-neck cells resulted in marked reduction in the number of parietal cells.

That the gastrointestinal inflammation did not result from direct infection with a contagious pathogen was suggested by four pieces of evidence. Stool cultures for aerobic bacteria yielded only normal fecal flora. Furthermore, rats of the 21-4L line and nontransgenic LEW rats were housed for long periods in the same cages with affected 21-4H rats without showing any diarrhea or other signs of illness. In addition, the histology of the gastrointestinal tract of the affected 21-4H rats was not consistent with any known infectious process. Finally, diarrhea is an almost invariable finding in the 33-3 line past the age of two months, and not in their nontransgenic littermates.

2. Peripheral and axial joints

Peripheral arthritis was observed in 10 of 14 21-4H males and in one of 9 21-4H females. This was manifested in most cases by swelling, erythema, and tenderness of the tarsal joints of one or both hindlimbs. In a few animals the carpal joints or digits were also inflamed. The arthritis persisted from a few days to several weeks, and in some cases showed an undulating pattern of remission and exacerbation.

Histologically, large accumulations of neutrophils were present in the joint space. The synovium was hyperplastic, edematous and infiltrated with large numbers of lymphocytes, plasma cells, and neutrophils, with neutrophils predominating in the most active lesions. There was marked pannus formation that eroded the bone at the synovial recess, invading and destroying the articular cartilage. Where the articular cartilage on adjacent joint surfaces was completely replaced by pannus, fibrous ankylosis occurred. Reactive bone formed small osteophytes along the diaphyses, and foci of metaplastic bone were seen within the fibrotic joint capsule. Chronic inflammation extended from the joint capsule to involve adjacent ligaments and tendons. Despite extensive joint destruction evident histologically, resolution generally occurred with preservation of mobility in the large joints.

Vertebral joints from two tails of 21-4H rats were examined histologically, and both revealed inflammatory changes at the outer aspects of the annulus fibrosus and its attachment to the vertebral endplate. The inflammatory cells consisted of lymphocytes and small numbers of plasma cells mixed with active fibroblasts. There was active bone resorption at the insertion of the annulus and the adjacent periosteum was reactive.

3. Skin and nails

Several animals of both sexes developed grossly evident changes in the tail skin and/or dramatic hyperkeratosis and dystrophy of the nails on all four extremities. Histologically, in the tail lesions the epidermis was massively thickened by psoriasiform hyperplasia. The rete ridges were regular and thickened at the base. Exocytosis of lymphocytes and neutrophils was common, with these cells accumulating in spongiotic foci in the epidermis, in the superficial parakeratotic crust, or around degenerated, necrotic keratinocytes. Diffuse orthokeratotic hyperkeratosis was prominent. The superficial papillary dermis contained a diffuse infiltrate of neutrophils, lymphocytes, and plasma cells. Similar changes were seen in skin over the distal aspect of the digits.

4. Testis and epididymis

Orchitis and epididymitis were prominent findings in the 21-4H males. The orchitis was manifested clinically by a progressive enlargement of the testes followed by testicular atrophy, with infertility supervening by three months of age in most of the males. In contrast, the females showed little loss of fertility, even in the presence of persistent diarrhea. Histologically, the testicular tunica was thickened by connective tissue, which contained active angioblasts and fibroblasts as well as large numbers of lymphocytes and plasma cells. The testes often contain numerous granulomas with necrotic centers surrounded by epithelioid macrophages, giant cells and peripherally by lymphocytes, plasma cells and fibrosis. Central infarction of the testis was a common finding in the most severely affected specimens.

The epididymis frequently contained granulomas similar to those found in the testis, along with dilated tubules containing necrotic cellular debris. The interstitium of the epididymis was expanded by lymphocytes, plasma cells, epithelioid macrophages, and moderate fibrosis.

5. Heart

Active inflammatory lesions were evident histologically in four of nine 21-4H hearts examined. In one specimen, extensive multifocal lesions were seen, involving the ventricular walls and septa. The lesions consisted of large numbers of macrophages admixed with lymphocytes and small numbers of plasma cells and eosinophils. The myofibers were widely separated by the inflammatory cells, and scattered karyorrhectic nuclei were seen. In the less severely affected specimens, infiltrates of lymphocytes and plasma cells were found at the root of the aortic valve. In more chronic lesions there was moderate fibrosis scattered throughout the myocardium accompanied by mild lymphocytic inflammation. In one animal the adventitia of the great vessels was infiltrated by large numbers of lymphocytes and plasma cells admixed with proliferating angioblasts and fibroblasts.

6. Eye and central nervous system

Mild keratitis and anterior uveitis were observed histologically in eyes from a couple of 21-4H rats, one of five eyes from 21-4L rats, and none of four eyes from nontransgenic LEW rats. These findings were judged to be nonspecific, probably secondary to bacterial keratitis.

A peculiar neurologic syndrome was seen in all of the females and most of the males of the 21-4H line. This was manifested by episodes of a stereotypical muscular dystonia, usually in response to handling or some other mild stimulus, that had the appearance of a generalized seizure. Electrophysiologic studies demonstrated increased muscular activity without evidence of a cortical seizure focus. For several reasons, this abnormality was thought to result from a process distinct from that giving rise to the other lesions. Whereas the other lesions appeared after puberty and then progressed, the neurologic abnormality began within a few weeks after birth and showed no increase in severity thereafter. Unlike the other disease processes, the clinical pattern of the neurologic findings showed little variation from rat to rat. Furthermore, the histologic abnormalities associated with the neurologic disease, which involved primarily the spinal cord and cerebellum, were not inflammatory. Finally, there was no evidence of neurologic disturbance in the transgenic F344 line that also showed diarrhea, nor in any of the other transgenic LEW lines.

7. Other Tissues

The following tissues were examined in at least one of the 21-4H rats showing diarrhea and found not to show histologic abnormalities: esophagus, lung, liver, kidney, adrenal, pancreas, penis, spleen, and thymus. Atrophy of thymus and spleen that was apparent to gross examination was a common finding, however, along with peripheral and mesenteric lymph node enlargement.

e. Clinical and Histologic Findings in Other Transgenic Lines

No clinical abnormalities were noted in any of the B27 transgenic LEW lines other than 21-4H. Histologic tissue surveys of several 21-4L rats revealed a mild degree of intestinal lymphoid hyperplasia and fibrosis as the only abnormality. Similar intestinal lesions were also found at a lower frequency in nontransgenic controls, and hence the significance of these findings in the 21-4L rats is not yet established. As noted above, almost all transgenic rats of the F344 line 33-3 showed diarrhea by two months of age. The 33-3 has also shown similar lesions of peripheral arthritis, genital inflammation, and skin changes. Axial skeletal changes and myocardial lesions have not yet been sought in this line.

f. Tissue Distribution of mRNA Expression

Figure 3A:
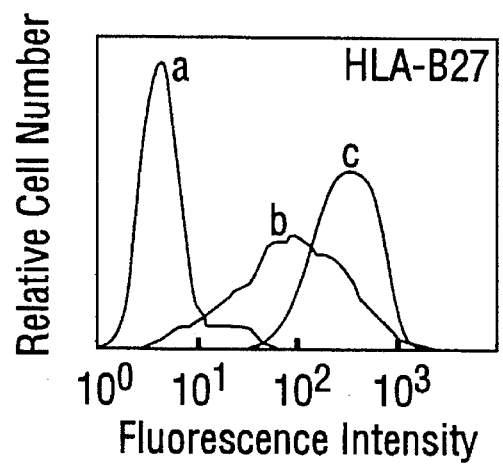
Figure 3B:
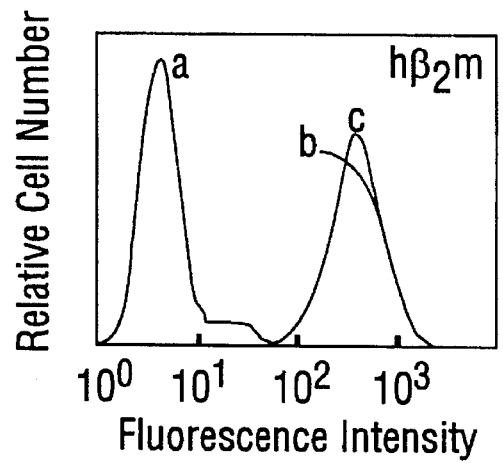
Figure 3C:
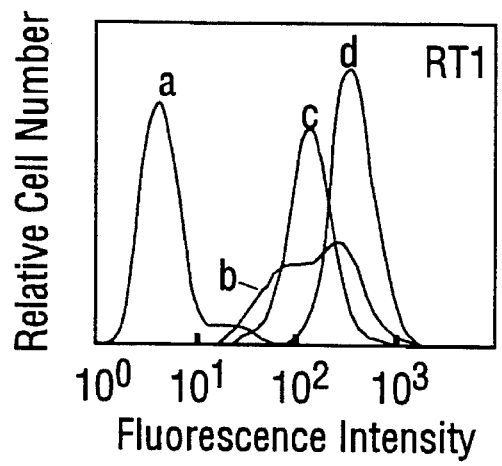

Despite the striking differences in disease manifestations, the 21-4H and 21-4L lines showed similar cell surface expression of the transgene products in PBL (Table 4, FIGS. 3A and 3B). It was thus of interest to compare the two lines with respect to the level and tissue distribution of mRNA transcripts of both transgenes. Northern blot analysis was carried out on total cellular RNA isolated from tissues of a limited number of rats of the 21-4H and 21-4L lines. HLA-B27 mRNA was detected with a 350 bp probe from the HLA-B 3' untranslated region (probe B in FIG. 2A), and h$\beta_2$m mRNA was detected with the same probe used to detect h$\beta_2$m genomic DNA (probe D in FIG. 2B). RT1 class I mRNA was detected with a 447 bp probe from the 3'-untranslated region of the RT1.A gene. FIGS. 4 and 5 contain results from age and sex matched representatives of the 21-4H and 21-4L lines and a nontransgenic control.

As shown in FIG. 4, the distribution and relative abundance of both B27 and h$\beta_2$m transgene transcripts among the various tissues examined were similar to those of the endogenous RT1 class I expression and typical of MHC class I gene expression (Klein 1986). In addition, both transgenes produced mRNA transcripts of the predicted size.

FIG. 5 shows direct comparisons of the 21-4H and 21-4L lines with respect to the relative amounts of B27 and RT1 transcripts in tissues affected by the disease process in the 21-4H line. The abundance of B27 transcripts was dramatically higher in the 21-4H rat than in the 21-4L rat in spleen, colon, and testis, and less markedly increased in jejunum and epididymis. In the thymus, the B27 transcripts were approximately equal in the two lines; however, this may have been a reflection of thymic atrophy in the 21-4H rats.

Although the apparent reduction of RT1 cell surface expression in PBL was comparable in 21-4H and 21-4L rats (FIG. 3C), at the level of mRNA there was no apparent reduction of RT1 transcripts in the 21-4L tissues examined. In contrast, the abundance of RT1 transcripts was markedly reduced in 21-4H spleen, thymus, and colon, compared with tissues from a nontransgenic rat. High expression of RT1 mRNA was found in the 21-4H testis and jejunum. In the case of testis, this probably reflects the intense infiltration of inflammatory cells seen histologically in this organ, whereas an explanation for the finding in jejunum is less apparent.

EXAMPLE II

Transgenic Animals Expressing HLA-DR4

This example is a prophetic disclosure of how one of skill in the art would proceed in the preparation of transgenic animals which express the HLA-DR4 gene. It is believed that by this procedure, one will be enabled to achieve an animal model of rheumatic arthritis. As with the introduction of HLA-B27, as disclosed in Example I above, it is believed that rats will be preferred for the preparation of an animal of rheumatoid arthritis using the HLA-DR4. Furthermore, other than the nature of the transgene which are introduced, the basic procedures which one would use in the preparation of DR4 expressing transgenic animals will be the same as set forth in Example I.

In order to create transgenic animals expressing DR4, subtype Dw4, one will desire to choose for microinjection two genomic cloned genes. One gene would comprise the DRA locus, encoding the DR alpha chain, preferably with flanking DNA of several kilobases both 5' and 3' of the exons. This could be obtained from a human genomic library with suitably large inserts (e.g., on the order of 30 to 50 kb) by screening the library with a DRA cDNA probe, then confirming the identity and size of the hybridizing clones by DNA sequencing and Southern blotting. An example of a suitable DNA segment for use as a DR alpha chain transgene would be the T9C cosmid described by Spies et al. (1985).

In addition to the DR alpha chain, one will desire to employ the DR4 beta chain, preferably a Dw4 subtype. As with the alpha chain, one will prefer to employ a segment which includes both the DR4,Dw4 allele of the DRB1 gene as well as DNA of several kilobases both 5' and 3' of the exons. The presence of flanking DNA is believed to be important because of the requirement for inclusion of cis-regulatory elements needed for appropriate tissue-specific expression.

A suitable DNA segment which includes the DR4,Dw4 allele of the DRB1 gene would preferably be obtained from a genomic library derived from a DR4,Dw4+ individual with rheumatoid arthritis, in order to ensure that any hitherto unidentified rheumatoid arthritis-specific sequences are included. A preferred means for preparing such a genomic library would be to start with high molecular weight DNA (Sambrook et al., 1989) prepared from leukocytes of a DR4,Dw4+ individual patient with severe seropositive rheumatoid arthritis (Arnett et al., 1988).

Once high molecular weight DNA is obtained in the foregoing manner from an affected individual, the DNA would then be sheared so as to produce fragments of average size 30-50 kb. The DNA would then be treated with BamHI methylase to block BamHI sites. Then BamHI linkers would be added, and the fragments ligated into a BamHI-cut cosmid vector such as pWE15, and packaged and amplified by suitable methods (Wahl et al., 1987). One will typically desire to prepare a library that has at least $5 \times 10^5$ independent clones in order to ensure that the desired gene will be represented.

One will then desire to probe the cosmid library in order to identify the clone or clones which incorporate the DR4, Dw4 allele. This would be achieved most readily, for example, using a cDNA probe encoding the DRB1 gene, followed by an oligonucleotide probe derived from the sequence of exon 2 of the DR4,Dw4 allele of the DRB1 gene (Freeman et al., 1987; Gao et al., 1990a, 1990b).

Once a positive clone is identified, one will desire to test it to ensure that it encodes the authentic DR4,Dw4 allele, e.g., by oligonucleotide hybridization, restriction mapping, and DNA sequencing. The DRA and DRB1 Dw4 clones could also be cotransfected into mouse L cells, and cells expressing an intact DR molecule would be detected by flow cytometry with the DR-specific monoclonal antibodies such as L243 (Lampson and Levy 1980; Shackelford et al., 1983).

Once the appropriate DNA segments are obtained, e.g., as described above, the isolated inserts would be microinjected into fertilized rat eggs just as described from the HLA-B27 and human β2m constructs in Example I. Integration of the microinjected DNA would be tested in the offspring by dot blot hybridization of tail DNA with probes derived from the 5' and 3' flanking regions of the two genes. Expression of the genes on lymphoid cell surfaces would be tested by flow cytometry, using DR-specific monoclonal antibodies such as L243. Tissue specific expression would be assessed by Northern blot hybridization, with probes derived from the 3'-untranslated regions of the two genes, or oligonucleotides derived from human-specific sequences within the exons of the two genes, as described for the B27 and human β2m genes (Hammer et al., 1990).

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, while the present invention is exemplified in terms of the introduction of a particular HLA-B27 transgene into rats, there is no reason why other HLA-B27 variants or allelic mutants could not be similarly employed so long as the variant gene was capable of conferring the desired trait. Similarly, whereas the present invention is exemplified in terms of a particular series of steps which the present inventors have found to work well in the context of the generation of transgenic rats, there is no reason why numerous modifications and alterations could not be made in these particular steps and nevertheless achieve the desired goal. All such modifications are intended to be included within the scope of the appended claims.

REFERENCES CITED

The following references are hereby incorporated by reference to the extent that they teach or explain or otherwise provide a basis for techniques or methodology which may be important in practicing the invention to its full extent as set forth in the appended claims.

Anderson, A. O. (1990). Structure and organization of the lymphatic system. In Immunophysiology. J. J. Oppenheim and E. M. Shevach, eds. (New York: Oxford University Press) pp. 14–45.

Armstrong, D. T. and Opavsky, M. A. (1988). Superovulation of immature rats by continuous infusion of follicle-stimulating hormone. Biol. Reproduct. 39, 511–518.

Arnett, F. C., Edworthy S. M., Bloch, D. A., McShane, D. J., Fries, J. F., et al. (1988). The American Rheumatism Association 1987 revised criteria for the classification of rheumatoid arthritis 31, 315–324.

Arnold, B. and Hämmerling, G. J. (1991) MHC Class-I transgenic mice. Ann. Rev. Immunol. 9:297–322.

Ball, J. (1971). Enthesopathy of rheumatoid and ankylosing spondylitis. Ann. Rheum. Dis. 30, 213–223

Benjamin, R. and Parham, P. (1990). Guilt by association: HLA-B27 and ankylosing spondylitis. Immunol. Today 11, 137–142.

Bergfeldt, L., Insulander, P., Lindblom, D., Möller, E. and Edhag, O. (1988). HLA-B27: an important genetic risk factor for lone aortic regurgitation and sever conduction system abnormalities. Am. J. Med. 85, 12–18.

Bjorkman, P. J., Saper, M. A., Samraoui, B., Bennett, W. S., Strominger, J. L. and Wiley, D. C. (1987a). The foreign antigen binding site and T cell recognition regions of class I histocompatibility antigens. Nature 329, 512-8.

Bjorkman, P. J., Saper, m. A., Samraoui, B., Bennett, W. S., Strominger, J. L. and Wiley, D. C. (1987b). Structure of the human class I histocompatibility antigen, HLA-A2. Nature. 329, 506-12.

Bodmer, J. G., Marsh, S. G., Parham, P., Erlich, H. A., Albert, E., Bodmer, W. F., Dupont, B., Mach, B., Mayr, W. R., Sasazuki, T. and al., e. (1990). Nomenclature for factors of the HLA system, 1989. Tissue Antigens. 35, 1-8.

Breur-Vriesendorp, et al. 1987. Distribution of HLA-B 27 subtypes in patients with ankylosing spondylitis: the disease is associated with a common determinant of the various B27 molecules. Ann. Rheum. Dis. 46:353

Brewerton, D. A., Gibson, D. G., Goddard, D. H., Jones, T. J., Moore, R. B., Pease, C. T., Revell, P. A., Shapiro, L. M. and Swettenham, K. V. (1987). The myocardium in ankylosing spondylitis. A clinical, echocardiographic, and histopathologic study. Lancet 1, 995–998.

Brewerton, D. A., Hart, F, De, Caffrey, M., Nicholls, A., James, D. C. O. and Sturrock, R. D. (1973). Ankylosing spondylitis and HL-A27. Lancet 1, 904–907.

Brinster, R. L., Chen, H. Y., Trumbauer, M. E., Yagle, M. K. and Palmiter, R. D. (1985). Factors affecting the efficiency of introducing foreign DNA into mice by microinjecting eggs. Proc. Natl. Acad. Sci. U.S.A. 82, 4438-42.

Brodsky, F. M., Bodmer, W. F. and Parham, P. (1979). Characterization of a monoclonal anti-beta 2-microglobulin antibody and its use in the genetic and biochemical analysis of major histocompatibility antigens. Eur J Immunol 9, 536-45.

Bulkley, B. H. and Roberts, W. C. (1973). Ankylosing spondylitis and aortic regurgitation. Description of the characteristic cardiovascular lesion from study of eight necropsy patients. Circulation 48, 1014–1027.

Calin, A., ed. (1984). Spondylarthropathies. Orlando, Grune & Stratton.

Chen, C. W. and Thomas, C. A. J. (1980). Recovery of DNA segments from agarose gels. Anal. Biochem. 101, 339–341.

Chen, J-H., D. H. Kono, Z Yong, M. S. Park, M. G. A. Oldstone, and D. T. Y. Yu. 1987. A Yersinia pseudotuberculosis protein which cross-reacts with HLA-B27. J. Immunol. 139: 3003

Cuvelier, C., Barbatis, C., Mielants, H., De Vos, M., Roels, H. and Veys, E. ( 1987 ). Histopathology of intestinal inflammation related to reactive arthritis. Gut 28, 394–401.

Duvic, M., Johnson, T. M., Rapini, R. P., Freese, T., Brewton, G., and Rios, A. (1987). Acquired immunodeficiency syndrome-associated Psoriasis and Reiter's Syndrome. Arch. Dermatol. 123, 1622–1632.

El-Zaatari, F., Sams, K. C. and Taurog, J. D. (1990). In vitro mutagenesis of HLA-B27. Amino acid substitutions at position 67 disrupt anti-B27 monoclonal antibody binding in direct relation to the size of the substituted side chain. J. Immunol. 144, 1512–1517.

Eulderink, F. (1990). Pathology of ankylosing spondylitis. Spine: State of the Art Reviews 4, 507–528.

Freeman, S. M., Noreen, H. J., Dahl, C. A., Nelson, P. J., Reinsmoen, N. L. and Bach, F. H. (1987). Determination of DRB alleles of DR4/Dw subtypes by oligonucleotide probing. Hum Immunol 20, 1–11.

Fukumoto, T., McMaster, W. R. and Williams, A. F. (1982). Mouse monoclonal antibodies against rat major histocompatibility antigens. Two Ia antigens and expression of Ia and class I antigens in rat thymus. Eur J Immunol 12, 237-43.

Gao, X. J., Fernandez, M., Shumway, W. and Stastny, P. (1990a). DNA typing for class II specific antigens with allele-specific or group-specific amplification. I. Typing for subsets of HLA-DR4. Human Immunol 27, 40–50.

Gao, X. J., Olsen, N. J., Pincus, T. and Stastny, P. (1990b). HLA-DR alleles with naturally occurring amino acid substitutions and risk for development of rheumatoid arthritis. Arthritis Rheum 33, 939-46.

Garrett, T. P., Saper, M. A., Bjorkman, P. J., Strominger, J. L. and Wiley, D. C. (1989). Specificity pockets for the side chains of peptide antigens in HLA-Aw68. Nature. 342, 692-6.

Good, A. E. (1974). Reiter's disease: a review with special attention to cardiovascular and neurologic sequelae. Semin. Arthritis Rheum. 3,253–286.

Granfors, K., Jalkanen, S., von Essen, R., Lahesmaa-Rantala, R., Isomaki, O., Pekkola-Heino, K., Merilahti-Palo, R., Saario, R., Isomaki, H., and Toivanen, A. ( 1989 ). Yersinia antigens in synovial-fluid cells from patients with reactive arthritis. N Engl J Med 320, 216-21.

Granfors, K., Jalkanen, S., Lindberg, A. A., Maki, I. O., von Essen, R., Lahesmaa-Rantala, R., Isomaki, H., Saario, R., Arnold, W. J. and Toivanen, A. (1990). Salmonella lipopolysaccharide in synovial cells from patients with reactive arthritis. Lancet ii, 685–688.

Greenwald, R. A. and Diamond, H. S. (1988). Handbook of Animal Models for the Rheumatic Diseases, Volume 1. Boca Raton, Fla., CRC Press.

Güssow, D., Rein, R., Ginjaar, I., Hochstenbach, F., Seemann, G., Kottman, A. and Ploegh, H. L. (1987). The human beta 2-microglobulin gene. Primary structure and definition of the transcriptional unit. J Immunol 139, 3132-8.

Hammer R. E., Maika, S. D., Richardson, J. A., Tang, J.-P. and Taurog, J. D. Spontaneous inflammatory disease in transgenic rats expressing HLA-B27 and human $\beta_2$-microglobulin. An animal model of HLA-B27-associated human disorders. Cell 63, 1099–1112.

Harris, E. D., Jr. ( 1990 ). Rheumatoid arthritis. Pathophysiology and implications for therapy. N Eng J Med 322, 1277-89.

Keat, A., J. Dixey, C. Sonnex, B. Thomas, M. Osborn, and D. Taylor-Robinson. 1987. *Chlamydia trachomatis* and reactive arthritis: the missing link. Lancet 1:72.

Keat, A. ( 1983 ). Reiter's syndrome and reactive arthritis in perspective. N Engl J Med 309, 1606-15.

Khan, M. A. (1988). Ankylosing spondylitis and heterogeneity of HLA-B27. Semin Arthritis Rheum 18, 134-41.

Khan, M. A. and van der Linden, S. M. (1990). Ankylosing spondylitis: clinical aspects. Spine: State of the Art Reviews 4, 529-551.

Kievits, F., Ivanyi, P., Krimpenfort, P., Berns, A. and Ploegh, H. L. (1987). HLA-restricted recognition of viral antigens in HLA transgenic mice. Nature 329, 447-9.

Klein, J. (1986). Natural History of the Major Histocompatibility Complex. NY, John Wiley & Sons.

Koller, B. H., Sidwell, B., DeMars, R. and Orr, H. T. (1984). Isolation of HLA locus-specific DNA probes from the 3'-untranslated region. Proc Natl Acad Sci U S A 81, 5175-8.

Krimpenfort, P., Rudenko, G., Hochstenbach, F., Guessow, D., Berns, A. and Ploegh, H. (1987). Crosses of two independently derived transgenic mice demonstrate functional complementation of the genes encoding heavy (HLA-B27) and light (beta 2-microglobulin) chains of HLA class I antigens. EMBO J 6, 1673-6.

Lampson, L. A. and Levy, R. (1980). Two populations of Ia-like molecules on a human B cell line. J Immunol 125, 293-9.

Lawrence, R. C., Hochberg, M. C., Kelsey, J. L., McDuffie, F. C., Medsger, T. A. Jr., Felts, W. R., and Shulman, L. E. (1989). Estimates of the prevalence of selected arthritic and musculoskeletal diseases in the United States. J Rheumatol 16, 427–441.

Lopez de Castro, J. A. (1989). HLA-B27 and HLA-A2 subtypes: structure, evolution and function. Immunol Today 10, 239–246.

Maika, S. D., Laimonis, L., Messing, A., Hammer, R. E. (1990). Genital hyperplasia and neoplasia in transgenic mice expressing HPV-18. Submitted.

McLean, L., Perrett, D., Winrow, V. R. and Archer, J. R. (1989). Status of an unpaired thiol group on the HLA-B27 epitope. Clin Exp Immunol. 77, 417-21.

Moll, J. M., Haslock, I., Macrae, I. F. and Wright, V. 1974. Associations between ankylosing spondylitis, psoriatic arthritis, Reiter's disease, the intestinal arthropathies, and Behcet's syndrome. Medicine (Baltimore). 53, 343-64.

Montanaro, A. and Bennett, R. M. (1984). Myelopathy in Reiter's disease. J Rheumatol 11, 540-1.

Nickerson, C. L., Luthra, H. L., Savarirayan, S. and David, C. (1990). Susceptibility of HLA-B27 transgenic mice to Yersinia enterocolitica infection. Human Immunol. 28, 382–396.

Parham, P., Lomen, C. E., Lawlor, D. A., Ways, J. P., Holmes, N., Coppin, H. L., Salter, R. D., Wan, A. M. and Ennis, P. D. (1988). Nature of polymorphism in HLA-A, -B, and -C molecules. Proc Natl Acad Sci U S A 85, 4005-9.

Peter, H. H. and Feldman, J. D. (1972). Cell-mediated cytotoxicity during rejection and enhancement of allogeneic skin grafts in rats. J Exp Med 135, 1301-15.

Rada, C., Lorenzi, R., Powis, S. J., van den Bogaerde, J., Parham, P. and Howard, J. C. (1990). Concerted evolution of class I genes in the major histocompatibility complex of murine rodents. Proc Natl Acad Sci U S A 87, 2167-71.

Raybourne, R. B., V. K. Bunning, and K. M. Williams. 1988. Reaction of anti-HLA-B monoclonal antibodies with envelope proteins of Shigella species. Evidence for molecular mimicry in the spondyloarthropathies. J. Immunol 140:3489.

Rebai, N. and Malissen, B. (1983). Structural and genetic analyses of HLA class I molecules using monoclonal xenoantibodies. Tissue Antigens 22, 107.

Sambrook, J., Fritsch, E. F., and T. Maniatis (1989). Molecular Cloning. A Laboratory Manual. 2nd edition. Cold Spring Harbor Laboratory Press.

Schlosstein, L., Terasaki, P. I., Bluestone, R. and Pearson, C. M. (1973). High association of an HL-A antigen, W27, with ankylosing spondylitis. New Eng. J. Med. 288, 704–706.

Schwimmbeck, P. L., D. T. Y. Yu, M. B. A. Oldstone. 1987. Autoantibodies to HLA-B27 in the sera of HLA-B27 patients with ankylosing spondylitis and Reiter's syndrome. J. Exp. Med. 166:173.

Shackelford., D. A., Lampson, L. A. and Strominger, J. L. (1983). Separation of three class II antigens from a homozygous human B cell line. J Immunol 130, 289-96.

Spies, T., Sorrentino, R., Boss, J. M., Okada, K. and Strominger, J. L. (1985). Structural organization of the DR subregion of the human major histocompatibility complex. Proc Natl Acad Sci U S A 82, 5165-9.

Stastny, P. (1978). Association of the B-cell alloantigen DRw4 with rheumatoid arthritis. N Eng J Med 298, 869–871.

Wahl, G. M., Lewis, K. A., Ruiz, J. C., Rothenberg, B., Zhao, J. and Evans, G. A. (1987). Cosmid vectors for rapid genomic walking, restriction mapping, and gene transfer. Proc Natl Acad Sci U S A 84, 2160-4.

Stieglitz, H., Fosmire, S. and Lipsky, P. (1989). Identification of a 2-Md plasmid from Shigella flexneri associated with reactive arthritis. Arthritis Rheum 32, 937-46.

Taurog, J. D. and Moore, P. M. (1986). An unusual motor neuropathy occurring in a patient with quiescent Reiter's disease. Clin. Exp. Rheum. 4, 147–149.

Taurog, J. D., Lowen, L., Forman, J. and Hammer, R. E. (1988a). HLA-B27 in inbred and non-inbred transgenic mice. Cell surface expression and recognition as an alloantigen in the absence of human beta 2-microglobulin. J Immunol 141, 4020-3.

Taurog, J. D., Argentieri, D. C. and McReynolds, R. A. (1988b). Adjuvant arthritis. Methods Enzymol. 162, 339–355.

Taurog, J. D. and El-Zaatari, F. A. K. (1988). In vitro mutagenesis of HLA-B27. Substitution of an unpaired cysteine residue in the alpha 1 domain causes loss of antibody-defined epitopes. J Clin Invest 82, 987-92.

Taurog, J. D. (1989). Genetics and immunology of the spondyloarthropathies. Curr. Opin. Rheumatol. 1, 144–150.

Taurog, J. D., Hammer, R. E., Maika, S. D., Sams, K. L., El-Zaatari, F. A. K., Stimpson, S. A. and Schwab, J. H. (1990). HLA-B27 transgenic mice as potential models of human disease. Transgenic Mice and Mutants in MHC Research. I. K. Egorov and C. S. David, eds., Berlin, Springer-Verlag, pp. 268–275.

Taurog, J. D. and Lipsky, P. E. (1990). Ankylosing spondylitis and reactive arthritis. In, Harrison's Principles of Internal Medicine. Wilson, J. D., Braunwald, E., Fauci, A. S., Isselbacher, K. J., Martin, J. B., Petersdorf, R. G., Root, R. K., eds. N.Y., McGraw-Hill, pp. 1451–1455.

Tiwari, L. and P. T. Terasaki. 1985. HLA and Disease Associations. Springer-Verlag, N.Y.

Toivanen, A. and Toivanen, P. (1988). Reactive Arthritis. Boca Raton, CRC Press.

Weiss, E. H., Schliesser, G., Kuon, W., Lang, M., Riethmueller, G., Kievits, F., Ivanyi, P. and Brem, G. (1990). Copy number and presence of human beta-2-microglobulin control cell surface expression of HLA-B27 antigen in transgenic mice with a 25 kb B27 gene fragment. Transgenic Mice and Mutants in MHC Research. Berlin, Springer-Verlag, pp. 205–213.

Yli-Kerttula, U-1. (1984). Clinical characteristics in male and female uro-arthritis or Reiter's syndrome. Clin. Rheumatol. 3, 351-60.

Yu, D. T., Choo, S. Y., Schaack, T. ( 1989 ). Molecular mimicry in HLA-B27-related arthritis. Ann Intern Med 111, 581-91.

Zoschke, D. and Segall, M. (1986). Dw subtypes of DR4 in rheumatoid arthritis: evidence for a preferential association with Dw4. Hum Immunol 15, 118-24.

What is claimed is:

1. A transgenic rat having incorporated into its genome a human HLA-B27 gene with the human $B_2$-microglobulin gene, said genes being present in said genome in a copy number effective to confer on said rat B27-associated inflammatory disease traits.

2. The transgenic of claim 1, which is a transgenic rat from a Fischer 344 or LEW rat line.

3. The transgenic rat of claim 2, which is a transgenic rat from a Fischer 344 rat line.

4. The transgenic rat of claim 3, which is a 33-3 rat.

5. The transgenic rat of claim 2, which is a transgenic rat from a LEW rat line.

6. The transgenic rat of claim 5, which is a 21-4H rat.

7. The transgenic rat of claim 1, wherein the human HLA-B 27 gene is the subtype HLA-B2705.

* * * * *